(12) United States Patent
Hansen et al.

(10) Patent No.: US 12,268,368 B2
(45) Date of Patent: Apr. 8, 2025

(54) MEDICAL VISUALISATION DEVICE

(71) Applicant: AMBU A/S, Ballerup (DK)

(72) Inventors: Jan Guldberg Hansen, Greve (DK); Kaspar Mat Matthison-Hansen, Helsingør (DK); Jonas Hjortlund, Copenhagen (DK); Felix-Johannes Abicht, Munich (DE); Günter Wilhelm Schütz, Augsburg (DE); Anja Katrin Dillinger, Aindling (DE)

(73) Assignee: AMBU A/S, Ballerup (DK)

( * ) Notice: Subject to any disclaimer, the term of this patent is extended or adjusted under 35 U.S.C. 154(b) by 561 days.

(21) Appl. No.: 17/666,316

(22) Filed: Feb. 7, 2022

(65) Prior Publication Data
US 2022/0151480 A1    May 19, 2022

Related U.S. Application Data

(63) Continuation-in-part of application No. PCT/EP2021/061289, filed on Apr. 29, 2021, and a (Continued)

(30) Foreign Application Priority Data

Apr. 30, 2020    (DE) ................... 10 2020 111 886.4
Apr. 30, 2020    (DK) ................... 2020 70273

(51) Int. Cl.
*A61B 1/273*    (2006.01)
*A61B 1/00*    (2006.01)
*A61B 1/05*    (2006.01)

(52) U.S. Cl.
CPC ........ *A61B 1/2736* (2013.01); *A61B 1/00098* (2013.01); *A61B 1/00165* (2013.01); *A61B 1/05* (2013.01)

(58) Field of Classification Search
CPC ... A61B 1/00098; A61B 1/00165; A61B 1/05; A61B 1/2736
See application file for complete search history.

(56) References Cited

U.S. PATENT DOCUMENTS 4,452,236 A    6/1984    Utsugi
4,573,450 A    3/1986    Arakawa
(Continued)

FOREIGN PATENT DOCUMENTS

CN    107361731 A    11/2017
CN    208017468 U    10/2018
(Continued)

OTHER PUBLICATIONS

German search report in patent application No. 10 2020 111 886.4, dated Apr. 30, 2020, 7 pages, and translation.
(Continued)

*Primary Examiner* — Aaron B Fairchild
(74) *Attorney, Agent, or Firm* — Faegre Drinker Biddle & Reath LLP

(57) ABSTRACT

A medical visualisation device including an instrument elevator having a guide surface for engagement with an instrument protruding through a tip part instrument channel and a X-ray transparent housing. The instrument elevator is radiopaque and pivotable around a pivot axis to adjust a guide angle between the guide surface and a longitudinal axis. The pivot axis being substantially perpendicular to the longitudinal axis and a viewing direction. A control wire being coupled to the instrument elevator to transfer a force exerted on the control wire to the instrument elevator to adjust the guide angle.

20 Claims, 18 Drawing Sheets

Related U.S. Application Data continuation-in-part of application No. PCT/EP2021/061001, filed on Apr. 27, 2021.

(56) References Cited

U.S. PATENT DOCUMENTS

| | | | |
|---|---|---|---|
| 4,841,949 A | 6/1989 | Shimizu et al. | |
| 5,201,908 A | 4/1993 | Jones | |
| 5,323,768 A | 6/1994 | Saito et al. | |
| 5,562,600 A | 10/1996 | Matsuno | |
| 5,569,162 A | 10/1996 | Komi | |
| 5,754,313 A | 5/1998 | Pelchy et al. | |
| 6,095,970 A | 8/2000 | Hidaka et al. | |
| 6,315,744 B1 | 11/2001 | Inaba | |
| 6,824,509 B2 | 11/2004 | Yamaya et al. | |
| 7,087,010 B2 | 8/2006 | Ootawara et al. | |
| 7,198,599 B2 | 4/2007 | Goto et al. | |
| 7,341,555 B2 | 3/2008 | Ootawara et al. | |
| 7,371,209 B2 | 5/2008 | Viebach et al. | |
| 7,413,543 B2 | 8/2008 | Banik et al. | |
| 7,662,094 B2 | 2/2010 | Iddan | |
| 7,922,650 B2 | 4/2011 | McWeeney et al. | |
| 7,955,255 B2 | 6/2011 | Boulais et al. | |
| 8,246,534 B2 | 8/2012 | Yamaya | |
| 8,313,427 B2 | 11/2012 | Ishii | |
| 8,485,966 B2 | 7/2013 | Robertson | |
| 8,986,194 B2 | 3/2015 | Ohara et al. | |
| 9,554,691 B2 | 1/2017 | Goldfarb et al. | |
| 9,566,502 B2 | 2/2017 | Takagishi et al. | |
| 9,655,502 B2 | 5/2017 | Levy et al. | |
| 9,822,287 B2 | 11/2017 | Yokoyama et al. | |
| 10,076,438 B2 | 9/2018 | Bendix et al. | |
| 10,517,470 B2 | 12/2019 | Hopkins, Jr. | |
| 10,980,558 B2 | 4/2021 | Ohki | |
| 11,064,866 B2 | 7/2021 | Yamaya | |
| 2001/0056224 A1 | 12/2001 | Renner et al. | |
| 2002/0175992 A1* | 11/2002 | Eino | A61B 1/00048 600/101 |
| 2004/0147807 A1 | 7/2004 | Viebach et al. | |
| 2005/0222493 A1* | 10/2005 | Kohno | A61B 1/00098 600/117 |
| 2006/0138309 A1 | 6/2006 | Wimmer | |
| 2007/0016077 A1 | 1/2007 | Nakaoka et al. | |
| 2007/0225554 A1* | 9/2007 | Maseda | A61B 1/018 600/128 |
| 2007/0249907 A1 | 10/2007 | Boulais et al. | |
| 2008/0004492 A1* | 1/2008 | Nakamura | A61B 1/0011 600/117 |
| 2008/0108869 A1 | 5/2008 | Sanders et al. | |
| 2008/0132760 A1 | 6/2008 | Takeuchi | |
| 2008/0300456 A1* | 12/2008 | Irion | A61B 1/0607 600/109 |
| 2009/0043166 A1 | 2/2009 | Ishii | |
| 2009/0067067 A1 | 3/2009 | Yamaya | |
| 2010/0286475 A1 | 11/2010 | Robertson | |
| 2011/0152618 A1* | 6/2011 | Surti | A61B 1/00137 600/129 |
| 2011/0288372 A1 | 11/2011 | Petersen | |
| 2011/0319717 A1 | 12/2011 | Pascal | |
| 2013/0172677 A1 | 7/2013 | Kennedy, II et al. | |
| 2013/0281779 A1 | 10/2013 | Robertson | |
| 2015/0005580 A1 | 1/2015 | Petersen | |
| 2016/0051126 A1 | 2/2016 | Troller et al. | |
| 2016/0157697 A1 | 6/2016 | Arai et al. | |
| 2016/0309993 A1 | 10/2016 | Hosogoe | |
| 2016/0363757 A1 | 12/2016 | Imai | |
| 2017/0049300 A1 | 2/2017 | Toyooka | |
| 2017/0078583 A1 | 3/2017 | Haggerty et al. | |
| 2017/0127915 A1 | 5/2017 | Viebach et al. | |
| 2017/0202436 A1 | 7/2017 | Chang | |
| 2017/0245734 A1 | 8/2017 | Kaneko | |
| 2017/0325671 A1 | 11/2017 | Hopkins, Jr. | |
| 2018/0078121 A1 | 3/2018 | Yasuda et al. | |
| 2018/0249895 A1 | 9/2018 | Calabrese et al. | |
| 2018/0303320 A1* | 10/2018 | Murayama | A61B 1/00165 |
| 2019/0246886 A1 | 8/2019 | Harada et al. | |
| 2019/0282070 A1 | 9/2019 | Vilhelmsen et al. | |
| 2020/0000314 A1 | 1/2020 | Larouche et al. | |
| 2020/0037860 A1 | 2/2020 | Yamaya | |
| 2020/0060520 A1 | 2/2020 | Sørensen et al. | |
| 2021/0169308 A1 | 6/2021 | Fukuzawa et al. | |
| 2021/0259522 A1* | 8/2021 | Ubbesen | A61B 1/00124 |
| 2023/0165451 A1 | 6/2023 | Dillinger et al. | |
| 2023/0277037 A1 | 9/2023 | Larouche et al. | |

FOREIGN PATENT DOCUMENTS

| | | |
|---|---|---|
| CN | 209951204 U1 | 1/2020 |
| DE | 3741938 A1 | 6/1988 |
| DE | 29613103 U1 | 10/1997 |
| DE | 19925323 A1 | 12/2000 |
| DE | 102008026537 A1 | 3/2009 |
| DE | 102015113020 A1 | 2/2017 |
| EP | 0591310 B1 | 4/1997 |
| EP | 1925252 A1 | 5/2008 |
| EP | 1421894 B2 | 2/2011 |
| EP | 2022389 B1 | 1/2012 |
| EP | 3153088 A1 | 4/2017 |
| EP | 3207852 A1 | 8/2017 |
| EP | 3243426 A1 | 11/2017 |
| EP | 3403566 A1 | 11/2018 |
| EP | 3583884 A1 | 12/2019 |
| JP | S55-166203 U | 11/1980 |
| JP | 02-278219 A | 11/1990 |
| JP | H04314439 A | 11/1992 |
| JP | H114804 A | 1/1999 |
| JP | 11-042201 A | 2/1999 |
| JP | 2000157486 A | 6/2000 |
| JP | 2001212074 A | 8/2001 |
| JP | 2002253484 A | 9/2002 |
| JP | 2003038416 A | 2/2003 |
| JP | 2006-239184 A | 9/2006 |
| JP | 2006-246933 A | 9/2006 |
| JP | 2013-081525 A | 5/2013 |
| JP | 2015-029764 A | 2/2015 |
| JP | 2015165839 A | 9/2015 |
| WO | 2004049921 A1 | 6/2004 |
| WO | 2015/084442 A1 | 6/2015 |
| WO | 2015/107801 A1 | 7/2015 |
| WO | 2017/025435 A1 | 2/2017 |

OTHER PUBLICATIONS

First examination report in related Danish application No. PA2020 70273, dated Aug. 11, 2020, 9 pages.

Second examination report in related Danish application No. PA2020 70273, dated Feb. 25, 2021, 4 pages.

Intention to grant related Danish application No. PA2020 70273, dated Apr. 23, 2021, 2 pages.

International search report and written opinion of related International application No. PCT/EP2021/061289, mailed Aug. 5, 2021, 12 pages.

International search report and written opinion of related International application No. PCT/EP2021/061001, mailed Sep. 13, 2021, 14 pages.

* cited by examiner

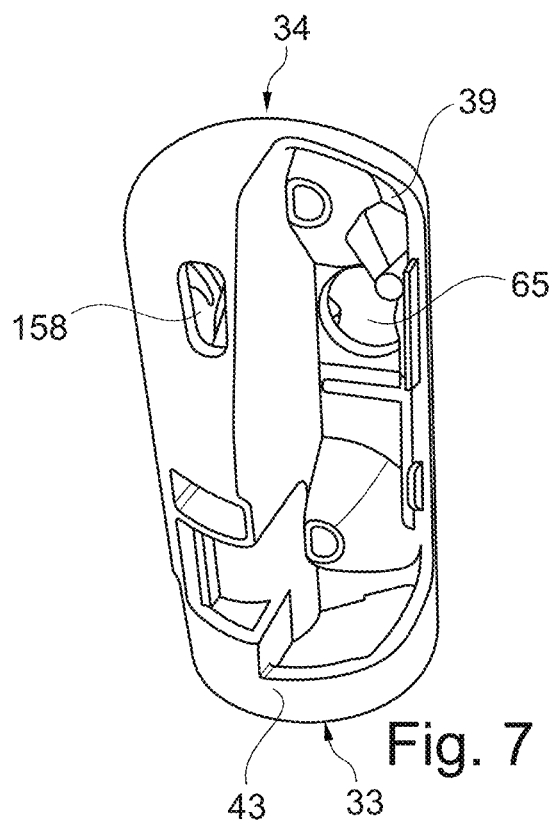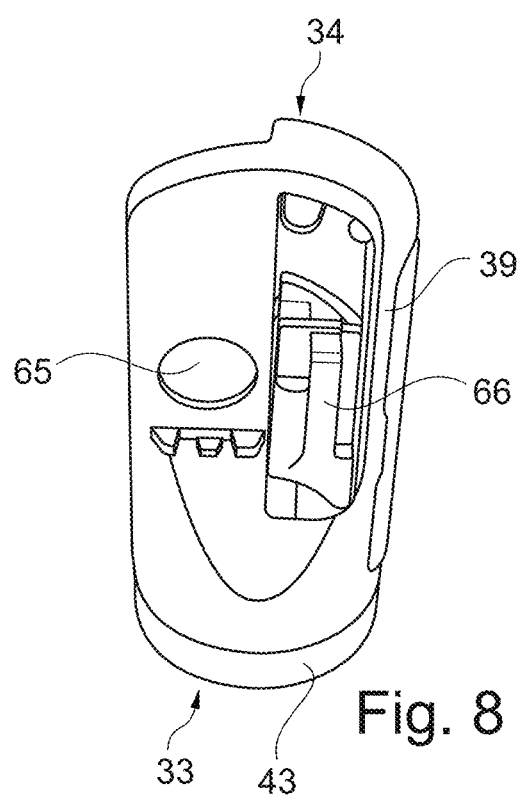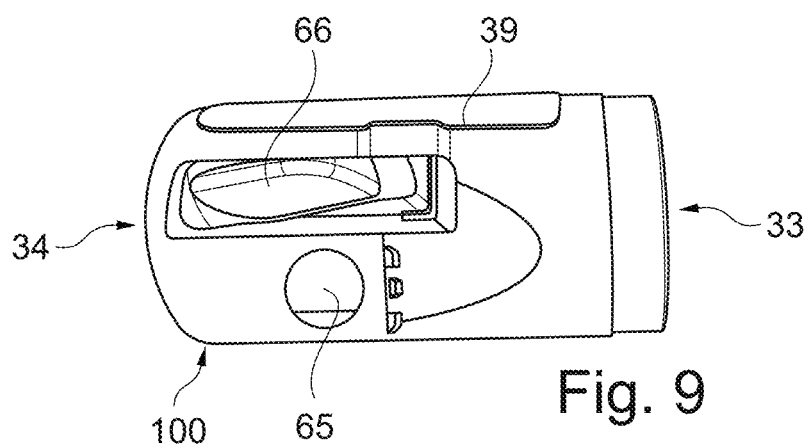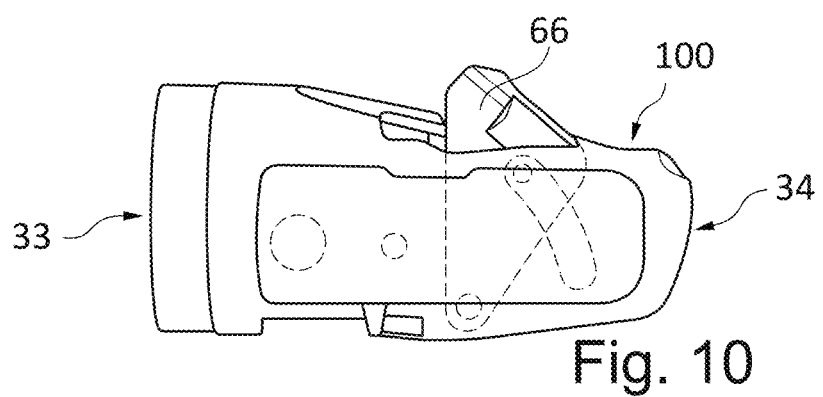

MEDICAL VISUALISATION DEVICE

CROSS-REFERENCE TO RELATED APPLICATIONS

This application is a continuation-in-part of International Patent Application No. PCT/EP2021/061001 filed Apr. 27, 2021 and titled "MEDICAL VISUALISATION DEVICE," which claims priority from and the benefit of Danish Patent Application No. PA202070273, filed Apr. 30, 2020 and issued Jan. 19, 2022 as Danish Patent No. DK 180719 B1, and is a continuation-in-part of International Patent Application No. PCT/EP2021/061289, filed Apr. 29, 2021 and titled "TIP FOR A SINGLE USE ENDOSCOPE, IN PARTICULAR FOR A SINGLE USE DUODENOSCOPE," which claims priority from and the benefit of German Patent Application No. 10 2020 111 886.4, filed Apr. 30, 2020. Said applications are incorporated herein by reference in their entirety.

TECHNICAL FIELD

The present disclosure relates to a medical visualisation device, such as an endoscope, more particularly a gastroscope, such as a duodenum endoscope. The present disclosure further relates to an instrument elevator and a tip part comprising such elevator, for an endoscope. The present disclosure also relates to a method for assembly of a medical visualisation device and/or parts thereof.

BACKGROUND

In endoscopes, such as a duodenum endoscope, e.g. for endoscopic retrograde cholangiopancreatography (ERCP) an elevator, alternatively denoted an instrument elevator, may be provided to adjust an angle of an instrument extending from the tip of the endoscope.

ERCP is a technique used to diagnose and treat certain problems of the biliary or pancreatic ductal systems. ERCP is used primarily to diagnose and treat conditions of the bile ducts and main pancreatic duct including gallstones, inflammatory strictures, leaks, and cancer. ERCP can be performed for diagnostic and therapeutic reasons.

ERCP may be performed using a side viewing endoscope, i.e. an endoscope where the view from the tip is angled, e.g. perpendicular, to the longitudinal axis of the endoscope tube. Also, the endoscope may comprise a side opening of a working channel, and an elevator, i.e. an instrument elevator, may be provided to adjust the angle of the instrument extending out through the side opening of the tip, to aid the operator to project the instrument to a specific area, such as to extend into the patient's bile papilla.

An elevator and its control means may be complex as it needs to be both small to fit into the endoscope and also needs to withstand a significant stress as the operator raises and lowers the elevator. Particularly for single-use endoscopes it may be challenging to provide a solution which balances the necessary strength with a cost enabling a disposable solution.

SUMMARY

It is an object of the present disclosure to provide solutions for providing an enhanced instrument elevator and/or an enhanced tip part comprising such elevator, which overcome or reduce at least some of the limitations of the prior art. Furthermore, it is an objective of the present disclosure to provide solutions, which may facilitate provision of a disposable endoscope comprising an instrument elevator.

Thus, the present disclosure relates to a medical visualisation device, such as an endoscope, more particularly a gastroscope, such as a duodenum endoscope. The present disclosure further relates to an instrument elevator and a tip part comprising such elevator, for an endoscope. The present disclosure further relates to a tip part housing that is radiotransparent and, optionally, the tip part comprises a radiopaque elevator. The present disclosure also relates to a method for assembly of a medical visualisation device and/or parts thereof.

Accordingly, an instrument elevator for a tip part of a medical visualisation device is disclosed. The instrument elevator has a guide surface for engagement with an instrument protruding through an instrument opening of the tip part. The instrument elevator is configured for adjusting the angle of the instrument by pivoting around a pivot axis.

Also, a medical visualisation device is disclosed. The medical visualisation device comprises a position interface, such as a handle, and an insertion tube extending from the position interface to a distal tube end. The insertion tube comprises a first channel, a second channel. A control wire extends through the second channel. The medical visualisation device comprises a tip part at the distal tube end. The tip part has a tip part housing extending from the distal tube end along a longitudinal axis. The tip part housing may be substantially cylindrical along the longitudinal axis.

The tip part comprises a window portion, e.g. forming part of a side wall of the tip part housing, and allowing a view from the interior of the tip part housing in a viewing direction being substantially perpendicular to the longitudinal axis, e.g. the viewing direction may be a radial direction. The window portion may consist essentially of a transparent material. Alternatively or additionally, the window portion may comprise an opening formed by the tip part housing.

The tip part further comprises a tip part instrument channel with an instrument opening defined by the tip part housing. The tip part instrument channel is coupled with the first channel of the insertion tube allowing an instrument being inserted through the first channel to protrude through the tip part instrument channel and distally out through the instrument opening.

The tip part further comprises an instrument elevator, such as the instrument elevator described above, having a guide surface for engagement with the instrument protruding through the tip part instrument channel. The instrument elevator is pivotable around a pivot axis to adjust a guide angle between the guide surface and the longitudinal axis. The pivot axis is substantially perpendicular to the longitudinal axis and the viewing direction. The control wire is coupled to the instrument elevator to transfer a force exerted on the control wire to the instrument elevator to adjust the guide angle.

A method for assembly of a medical visualisation device, such as the herein described medical visualisation device, is also disclosed.

BRIEF DESCRIPTION OF THE FIGURES

Embodiments of the disclosure will be described in more detail in the following with regard to the accompanying figures. The figures show one way of implementing the present disclosure and are not to be construed as being limiting to other possible embodiments falling within the scope of the attached claim set.

FIGS. 7-12 are perspective and side views of the tip part of FIG. 6;

DETAILED DESCRIPTION

Figure 1:
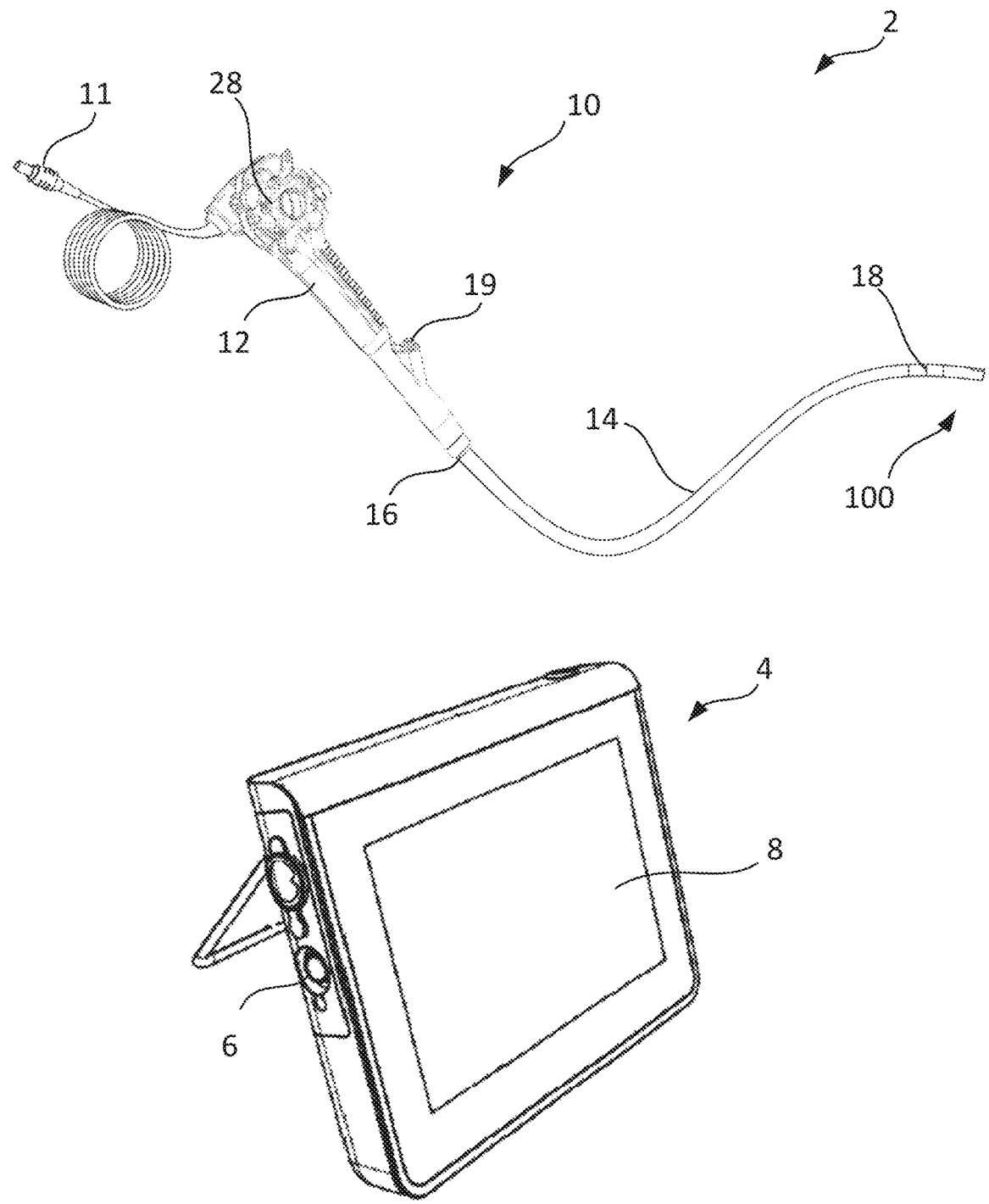
FIG. 1 is a perspective view of an embodiment of a visualisation system.

The insertion tube of the medical visualisation device may be at least partly flexible. For example, the insertion tube may comprise a bendable section, e.g. near the distal end of the insertion tube. The bendable section may be operated to direct the distal tube end and/or the tip part in a desired direction. The medical visualisation device may comprise one or more control knobs operable to direct the distal tube end and/or the tip part in a desired direction, e.g. by bending of the bendable section.

The tip part may comprise a camera arranged to look through the window portion in the viewing direction. Alternatively, optical fibres may be provided, e.g. arranged through the insertion tube, to transfer an image of the view through the window portion to a camera sensor arranged remotely from the window portion, e.g. in the handle. The tip part may comprise one or more light sources, e.g. LEDs, for providing illumination in the viewing direction. The insertion tube may comprise one or more electrical conductors, e.g. to transmit a camera signal indicative of image data generated by the camera through the insertion tube and/or to provide signals to the light sources to increase or decrease illumination.

The instrument elevator may be pivotable between a lowered position and a raised position. In the lowered position the guide angles may be minimized. In the raised position the guide angle may be maximized. The instrument elevator may be pivoted between 50-90 degrees, such as between 60-80 degrees, such as about 70 degrees, between the lowered position and the raised position.

The instrument elevator may be made substantially of polymer, such as polyoxymethylene (POM), and preferably at least 70, 80, and 90% POM. POM is particularly advantageous as it facilitates a low friction guide surface. The tip part may be made of a polymeric material, such as a thermoplastic elastomer (TPE), such as Styrene Butadiene Copolymer (SBC), e.g. K-resin.

The control wire may be a high strength steel wire. The control wire may have a wire diameter, e.g. between 0.3-0.5 mm, such as 0.4 mm.

The control wire may be a solid wire, alternatively denoted a monofilament wire. Utilizing a control wire may increase the buckling strength of the wire, thus improving pushing performance and reduce the risk of the wire curling up upon pushing. It is a further advantage of the solid wire that it may aid in reducing the wire diameter. Furthermore, the use of a solid wire reduces the risk of the wire curling up inside the tip housing.

The control wire may extend from a proximal end to a distal end. The proximal end may be arranged at the handle. The distal end may be arranged at the instrument elevator. The control wire may comprise a distal portion extending to the distal end, e.g. from an intermediate position of the control wire. The control wire may have a primary segment and a secondary segment. Additionally, the control wire may comprise a tertiary segment. The distal portion of the control wire may comprise the secondary segment and/or the tertiary segment. The secondary segment may be between the primary segment and the secondary segment. The primary segment and the tertiary segment may be substantially parallel. The secondary segment may be substantially parallel to the pivot axis.

The control wire may comprise a first bend between the primary segment and the secondary segment. The control wire may comprise a second bend between the secondary segment and the tertiary segment.

The first bend may be between 80-100 degrees, such as between 85-95 degrees, such as 90 degrees. The second bend may be between 80-100 degrees, such as between 85-95 degrees, such as 90 degrees. The angle of the bends may denote the change of direction of the control wire, i.e. 0 degrees is equivalent to no bend, while 180 degrees is equivalent to a U-shaped bend.

The first bend may have a minimum radius of curvature between 0.1-0.5 mm. The second bend may have a minimum radius of curvature between 0.2-1.5 mm. The second bend may have a minimum radius of curvature bigger than the minimum radius of curvature of the first bend.

The instrument elevator may comprise a coupling part. The coupling part may have a conduit. The primary segment may be arranged on a first side of the coupling part along the pivot axis. The secondary segment may extend through the conduit. The tertiary segment may be arranged on a second side of the coupling part. The second side may be opposite the first side of the coupling part along the pivot axis.

By providing the bend(s) on the sides of the coupling part of the instrument elevator and threading the control wire through the conduit of the coupling part, the control wire may be coupled to the instrument elevator.

The tip part may comprise a sleeve element, e.g. enclosing the secondary segment and/or the tertiary segment of the control wire. The sleeve element may be metal. The sleeve element may provide increased stiffness to the control wire. The control wire may further restrict the control wire from being pulled out of the conduit of the instrument elevator.

The sleeve element may be secured to the control wire by compression of one or more portions of the sleeve element enclosing a portion of the control wire, e.g. with a crimping tool. For example, the sleeve element may be secured to the secondary segment by compression of a first portion of the sleeve element enclosing at least a portion of the secondary segment, such as a proximal or distal end of the secondary segment. Alternatively or additionally, the sleeve element may be secured to the tertiary segment by compression of a second portion of the sleeve element enclosing at least a portion of the tertiary segment, such as a proximal or distal end of the tertiary segment.

It is particularly advantageous to secure (or primarily secure) the sleeve element to tertiary segment, in particular to the distal end of the tertiary segment, as the stress at a more distal position is reduced, due to the sleeve and bends taking absorbing some of the wire stress, compared to a more proximal position. Thereby, any minor reduction in wire stress caused by damages caused by the compression of the sleeve, may be less critical, as the experienced stress is submaximal.

The sleeve element and the control wire may be bent together, e.g. during forming of the second bend, and such that the sleeve element encloses the second bend. Thereby, the control wire may be protected by the sleeve element to prevent breaking of the wire. Thus, the sleeve element may be attached to the control wire prior to performing the second bend.

It is an advantage of fixating the wire by bends and/or a sleeve as described that thermal solutions, e.g. welding or soldering may be avoided, thereby reducing variance in fixation strength caused by heating of the materials. Providing for a more reliable and predictable strength of the coupling.

Because the instrument elevator is located near the window portion, and therefore close to the field of view, and in some positions within the field of view from the window portion. The instrument elevator may be found to affect the view through the window portion. For example, the instrument elevator may reflect or absorb light, resulting in overexposure or underexposure of images, e.g. captured by the camera. Therefore, the inventors have found that it will be advantageous to provide the instrument elevator, such as the guide surface of the instrument elevator, in a colour which balances the reflected light. Thus, the instrument elevator, such as the guide surface, has an elevator colour. The elevator colour may be a grey colour, e.g. a colour with $L^*$ between 15 to 75, $a^*$ between negative 10 to positive 10, such as between negative 5 and positive 5, such as 0, and $b^*$ between negative 10 to positive 10, such as between negative 5 and positive 5, such as 0, as measured by a CIEL$^*$a$^*$b$^*$ colour code system. In the CIEL$^*$a$^*$b$^*$ system $L^*$ is a measure of lightness from black (0) to white (100), $a^*$ is a measure of green/red from green (negative 100) to red (positive 100), and $b^*$ is a measure of blue/yellow from blue (negative 100) to yellow (positive 100). One particular example of the elevator colour may be CIEL$^*$a$^*$b$^*$ (34.33, −3.97, −6.66), which may be equivalent to Pantone 425c, or CMYK (63, 51, 45, 33).

The instrument elevator may comprise an X-ray detectable material, such as a radiopacity agent. For example, the instrument elevator may be made of a material, such as POM, comprising a radiopacity agent. A radiopacity agent may be any agent capable of stopping or reducing passage of X-rays. Some exemplary radiopacity agent may be barium sulphate, tungsten and stainless steel. However, any known radiopacity agent or X-ray detectable material may be used. A combination of a plurality of different radiopacity agents may be used. By providing the instrument elevator with an X-ray detectable material, the instrument elevator may be visible on an X-ray image of a patient during a procedure using the medical visualisation device. Thereby, an X-ray image may be used to guide and/or confirm the position and/or orientation of the instrument elevator inside the patient.

The tip part may comprise an axle extending along the pivot axis. The instrument elevator may comprise an axle opening adapted to receive the axle. The axle of the tip part may extend through the axle opening of the instrument elevator. The instrument elevator may be adapted to pivot around the axle.

The tip part may comprise an intermediate wall separating the tip part instrument channel and a control wire compartment. The control wire compartment may be coupled with the second channel of the insertion tube. The intermediate wall may define an intermediate wall opening, e.g. a semicircular opening, between the tip part instrument channel and the control wire compartment. The control wire may extend through the control wire compartment and through the intermediate wall opening to the instrument elevator in the tip part instrument channel.

The control wire compartment may comprise a ceiling surface, e.g. between the distal tube end and the intermediate wall opening along the longitudinal axis. The ceiling surface may be configured for engagement with the control wire, e.g. to limit deflection of the control wire in the viewing direction, and to transfer a pushing force exerted on the control wire, which may result in the control wire being deflected, to the instrument elevator to minimize the guide angle.

The tip part housing may comprise a secondary opening between the tip part instrument channel and the exterior of the tip part housing. The secondary opening may be provided opposite the instrument opening, e.g. along the viewing direction.

The instrument elevator may comprise a protruding wall, e.g. opposite the guide surface. and wherein the protruding wall blocks part of the secondary opening when the instrument elevator is in the lowered position. The protruding wall may comprise a surface area smaller than the area of the secondary opening. The protruding wall may be provided to facilitate breaking of, e.g., gallstones having entered into the housing. Thus, the protruding wall may be denoted a gallstone breaking element. The secondary opening allows fragments, e.g. of broken gallstones, to be pushed out of the housing, to ensure that the instrument elevator is not prevented from being positioned in the lowered position. The surface area of the protruding wall may be smaller than 1 $mm^2$, such as smaller than 0.50 $mm^2$, such as smaller than 0.4 $mm^2$. The surface area of the secondary opening may be between 3-8 $mm^2$, such as between 4-6 $mm^2$, such as approximately 5 $mm^2$.

The instrument elevator may comprise one or more support points, e.g. including a first support point and/or a second support point, to prevent rotation of the instrument elevator about the longitudinal axis and/or about the viewing direction. The first support point may be on the first side of the instrument elevator along the pivot axis. The second support point may be on the second side of the instrument elevator along the pivot axis. The second side of the instrument elevator may be opposite the first side of the instrument elevator. The first support point may be arranged to contact a first sidewall of the tip part instrument channel and/or the second support point may be arranged to contact a second sidewall of the tip part instrument channel, e.g. for all positions of the instrument elevator between the lowered position and the raised position. The second sidewall may be opposite the first sidewall. A distance between the distal tube end and the first support point may be larger than a distance between the distal tube end and the conduit of the instrument elevator. A distance between the distal tube end and the second support point may be smaller than a distance between the distal tube end and the conduit of the instrument elevator.

The disclosed method for assembly of the medical visualisation device may comprise providing a tip part housing, such as the tip part housing as described above, wherein the tip part instrument channel is couplable to the first channel of the medical visualisation device. The method further comprises providing an instrument elevator, such as the instrument elevator as described above, and providing a control wire such as the control wire described above.

The method comprises coupling the distal portion, e.g. the secondary segment and/or the tertiary segment, of the control wire to the instrument elevator, such as to the coupling part of the instrument elevator.

Coupling the distal portion of the control wire to the instrument elevator may comprise inserting the control wire through the conduit of the coupling part of the instrument elevator, e.g. such that the primary segment of the control wire is arranged on the first side of the coupling part and the secondary segment of the control wire is extending through the conduit, and optionally such that the tertiary segment of the control wire is arranged on the second side of the coupling part.

Coupling the distal portion of the control wire to the instrument elevator may comprise bending the control wire to obtain the first bend between the primary segment and the secondary segment and/or the second bend between the secondary segment and the tertiary segment.

Coupling the distal portion of the control wire to the instrument elevator may comprise securing a sleeve element, such as the sleeve element as described above, to the distal portion of the control wire such that the distal portion of the control wire is enclosed by the sleeve element. Securing the sleeve element to the distal portion of the control wire may comprise compressing, e.g. with a crimping tool, a portion, such as the first portion and/or the second portion, of the sleeve element enclosing at least a portion of the distal portion of the control wire. The sleeve element may be secured to the distal portion of the control wire prior to bending the control wire to obtain the second bend. Bending the control wire to obtain the second may include concurrently bending the sleeve element and the control wire to obtain the second bend.

The sleeve element may be secured prior to bending the control wire. The second bend, e.g. concurrently bending the sleeve element and the control wire, may be provided after securing the sleeve element. The control wire, and optionally the sleeve element, may be inserted through the conduit of the coupling part after the second bend has been provided. The first bend may be provided after inserting the control wire through the conduit of the coupling part, i.e. while the control wire and the sleeve element is extending through the conduit.

After coupling the distal portion of the control wire to the instrument elevator, the method comprises passing the control wire through the instrument opening of the tip part housing, and optionally through the first channel of the insertion tube, in a proximal direction, and inserting the instrument elevator together with the distal portion of the control wire through the instrument opening of the tip part housing, to position the instrument elevator in a seat for the instrument elevator in the tip part instrument channel. Upon insertion into the seat, the instrument elevator may snap into place and may be retained by the tip part housing. The instrument elevator and the distal portion of the control wire may be inserted through the instrument opening when the remainder of the control wire has been passed through the instrument opening. Hence, the control wire and the instrument elevator may follow each other through the instrument opening in the proximal direction.

Passing the control wire through the instrument opening of the tip part housing may include passing the control wire through the intermediate wall opening and through the control wire compartment of the tip part housing.

The method may comprise inserting the axle through the axle opening of the instrument elevator, e.g. after inserting the instrument elevator together with the distal portion of the control wire through the instrument opening. Insertion of the axle may lock the instrument elevator in its position. The axle opening of the instrument elevator may be aligned with an axle opening of the tip part housing, and the axle may be inserted through the axle opening of the tip part housing and the axle opening of the instrument elevator. The axle opening of the tip part housing may be provided in the intermediate wall separating the top part instrument channel and the control wire compartment. A sidewall element may be provided comprising the axle, and the method may comprise attaching the sidewall element to the tip part housing including inserting the axle through the axle opening of the instrument elevator and/or through the axle opening of the tip part housing.

The method may further comprise providing a handle and an insertion tube, such as the handle and insertion tube as described above. The method may comprise attaching the tip part housing to the distal tube end.

The control wire may extend through the second channel of the insertion tube prior to coupling the distal portion of the control wire to the instrument elevator. The method may comprise threading the distal end of the control wire through the instrument opening of the tip part housing, optionally through the control wire compartment and through the intermediate wall opening, in a distal direction prior to coupling the distal portion of the control wire to the instrument elevator. After coupling the distal portion of the control wire to the instrument elevator the control wire may be reversed and passed back through the instrument opening in the proximal direction.

Alternatively, the method may comprise, after coupling the distal portion of the control wire to the instrument elevator, threading the proximal end of the control wire through the instrument opening of the tip part housing, optionally through the intermediate wall opening and through the control wire compartment, in a proximal direction. After threading the proximal end of the control wire through the instrument opening, the remainder of the control wire may follow and be passed through the instrument opening in the proximal direction.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Figure 2:
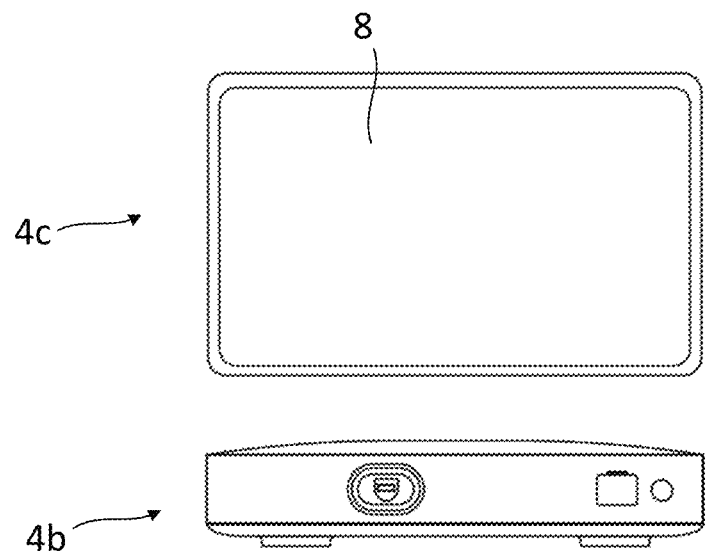
FIG. 2 is a front view of a monitor device operable in the visualization system of FIG. 1.

FIG. 1 is a schematic diagram illustrating an exemplary visualisation system 2 comprising an exemplary medical visualisation device 10 and an exemplary monitor device 4 having a display 8 operable to present an image representative of a view of a camera in the tip part 100 of the visualisation device 10. Example medical visualisation devices include endoscopes and variations thereof including duodenoscopes. The medical visualisation device 10 is communicatively connected to the monitor device 4 via a cable having a device connector 11 that is inserable in a monitor connector 6 of the monitor device 4. A variation of the monitor device 4, denoted by numeral 4b, is shown in FIG. 2, where a display device 4c includes the display 8. The monitor device 4b can be connected, wirelessly or via a cable, with the display device 4c. The medical visualisation device 10 and the monitor device 4, 4b can also include transceivers to communicate images and configuration data between them wirelessly, for example via a wireless HDMI protocol. The visualisation system 2 is operable to present live images generated by the medical visualisation device 10 with the display 8.

The visualisation device 10 comprises a handle 12 and an insertion tube 14. The insertion tube, or insertion cord, 14 extends from the handle 12, e.g. a proximal tube end 16, to a distal tube end 18. The medical visualisation device 10 comprises the tip part 100 at the distal tube end 18. The insertion tube 14 may be at least partly flexible, and may comprise a bendable section, which may be operated to direct the distal tube end 18 and the tip part 100 in a desired direction. The medical visualisation device 10 may comprises a control knob 28 (or knobs), as illustrated, which may be operated to direct the distal tube end 18 and the tip part 100 in the desired direction.

The handle can be considered a position interface between user and the cord or insertion tube 14. The function of the handle is for the operator of the medical visualization device to grasp the handle to position the insertion tube 14 in the appropriate place. The handle also functions to provide control knobs, actuators, ports, etc., for controlling the position of the tip part and instruments guided through the insertion tube. Alternatively, a different position interface can be provided that is connected to the insertion tube 14 and removably attaches to a robotic arm. The insertion tube, or insertion cord, 14 thus extends from the robotic arm and the medical visualization device remains detachable from the robotic arm and disposable. The tip part 100 and the elevator instrument 66, 200 (described below) are the same regardless of the position interface used. The robotic arm responds to signals, including voice commands, from the operator to rotate, translate, and otherwise position the proximal end of the insertion cord, as an operator would do manually. The proximal end of the control wire 30 would then be connected to an actuator operable to translate the wire. Example actuators include single axis actuators such as linear motion actuators, in some examples including a threaded rod coupled to a threaded nut portion rotatable by a motor. In other examples a slider type actuator may be used. The motor is controlled in the same manner as the robotic arm, via signals initiated by the operator. Rotation clockwise or counterclockwise translates the wire to and fro.

The medical visualisation device 10, e.g. the handle 12, comprises an instrument port 19, connected with a first channel of the insertion tube 14 (see FIG. 3), thereby allowing an instrument to be inserted through the instrument port 19 to protrude through the insertion tube 14 to the tip part 100.

The visualisation device 10 comprises a device connector 11 configured to be received by a monitor connector 6 of the monitor device 4, such as to allow display, on a display 8 of the monitor device 4, of an image representative of a view of a camera in the tip part 100 of the visualisation device 10.

Figure 3:
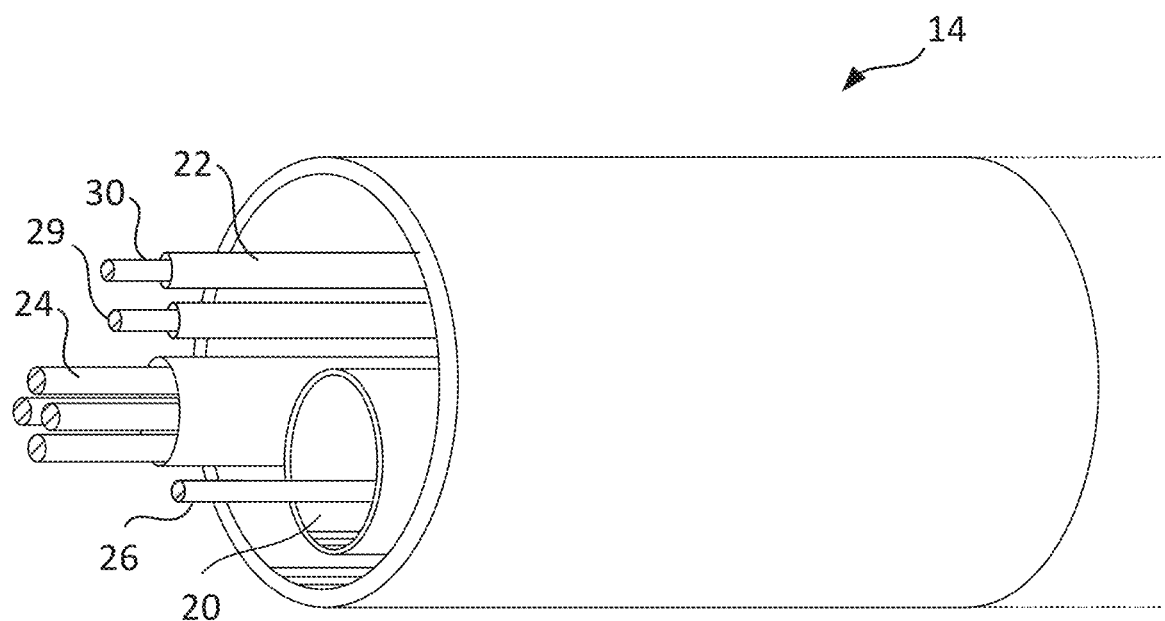
FIG. 3 is a perspective view of an exemplary insertion tube.

FIG. 3 is a schematic diagram illustrating an exemplary insertion tube 14, such as the insertion tube of the visualisation device 10 as illustrated in FIG. 1.

The insertion tube 14 comprises a first channel 20 and a second channel 22. The first channel 20 is configured for receiving an instrument 26 being inserted from the handle of the visualisation device and extending to the tip part. For example, an instrument may be inserted through the first channel 20 and used to take samples of tissue, i.e. biopsies, near the tip part. A pull or steering wire 29 extending through the insertion tube from one of the knobs to the tip, whereby rotation of the knob translates the steering wire 29 causing the bending section to bend. Additional steering wires may be added for one or two dimensional steering. A control wire 30 is extending through the second channel 22. The control wire 30 may be a solid wire, such as a monofilament wire. For example, the control wire 30 may be a high strength steel wire. The insertion tube 14 may comprise channels in addition to those shown. For example, the insertion tube 14 may comprise steering wires for control of a bendable section of the insertion tube 14. However, for simplicity, these are omitted from the present schematic illustration. Also, some of the illustrated channels may be omitted by arranging some of the elements directly in the lumen of the insertion tube 14. For example, the control wire 30 may be arranged directly in the lumen, whereby the lumen may constitute the second channel 22 through which the control wire 30 extends.

The insertion tube 14 comprises one or more electrical conductors 24 (here illustrated as one wire, optionally comprising several conductors) to transmit a camera signal indicative of image data generated by a camera through the insertion tube 14, e.g. from the tip part to the handle and optionally to a display connected to the handle, as described above. The electrical conductors 24 may also be utilized to control light sources at the tip part, such as to illuminate an area in front of the camera. In alternative exemplary visualisation devices, the insertion tube may comprise optical fibres instead of the electrical conductors 24, such as to facilitate transmission of light between the tip part and the handle.

Figure 4:
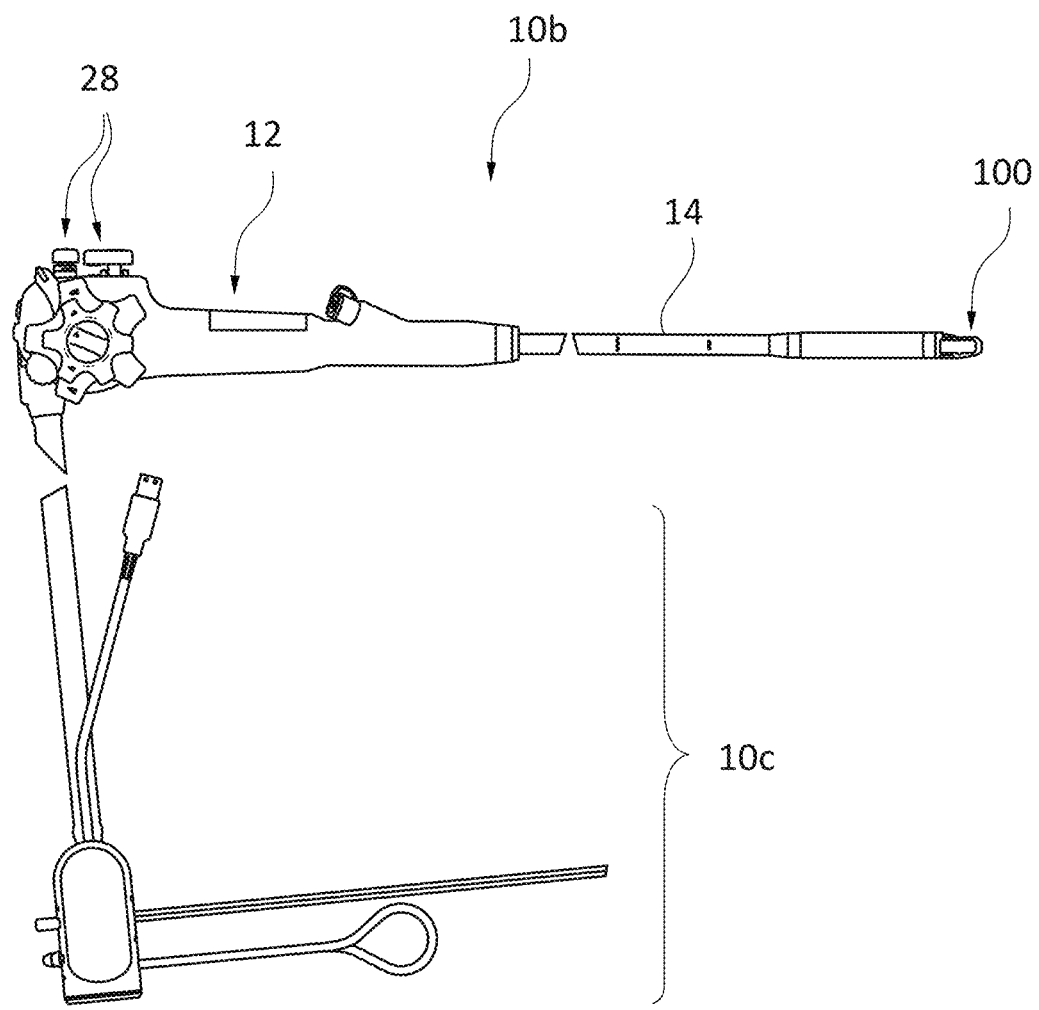
FIGS. 4 and 5 are side views of an embodiment of a medical visualisation device operable in the visualization system of FIG. 1.
Figure 5:
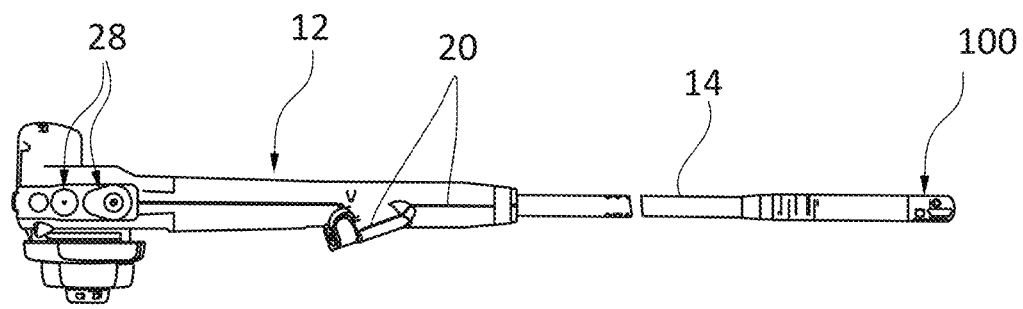

FIGS. 4 and 5 show an example medical visualisation device, or endoscope, 10b, which is preferably a single use endoscope (duodenoscope) and comprises a connector unit 10c for connecting the endoscope 10b with a (separate)

supply unit, which may also be referred to as a base unit, for at least one operating resource (for example, electric power, water, etc.). The endoscope 10b further comprises a supply line located proximal (in the direction toward the user) to/at the connector unit. The supply line is for supplying said at least one operating resource from the connector unit to the endoscope handle 12 which is designed to be held by an user and—in accordance with the manual actuations of several control knobs 28 at the handle 12 by the user—from the handle 12 to a distal (direction away from the user/direction toward the patient) tip part 100 (shown in FIG. 1), which is intended to be inserted into a patient's body cavity and which is located at the distal end of the insertion tube 14. The insertion tube 14 comprises at least one working channel 20 (as described with reference to FIG. 3) having an opening in the tip part 100 such that a surgical instrument can be shifted through the working channel to extend beyond the tip part 100 into a distal and/or radial direction.

Figure 6:
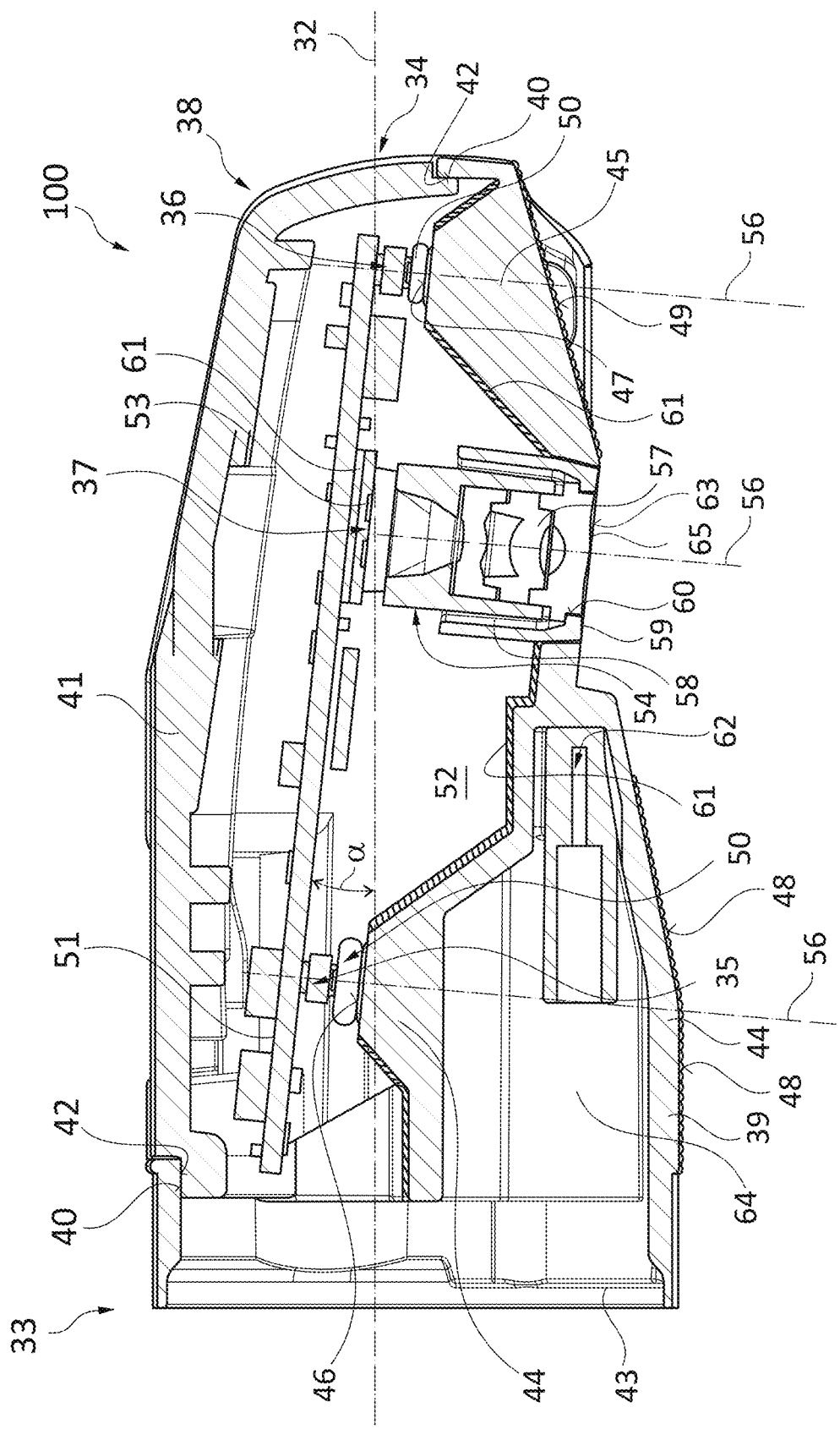
FIG. 6 is a sectional view of an embodiment of a tip part.
Figure 11:
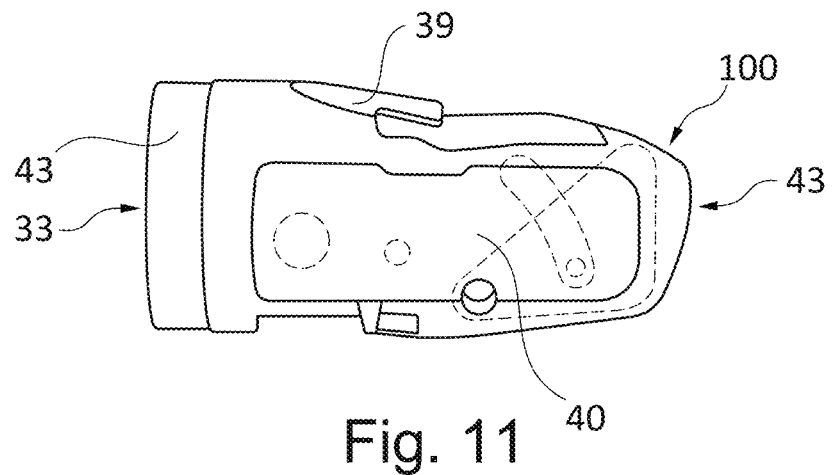
Figure 12:
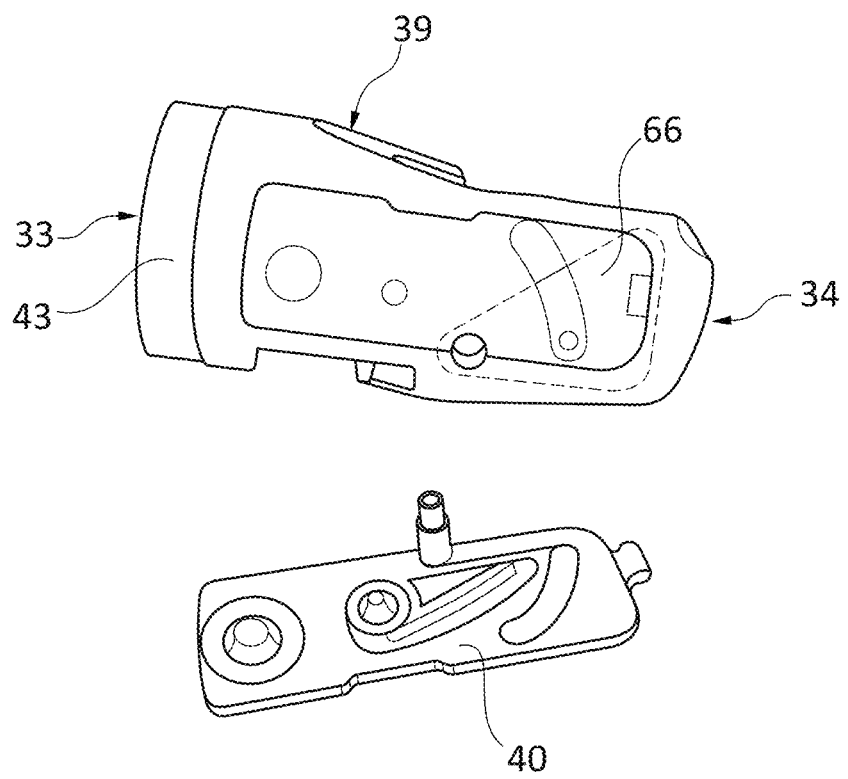

FIG. 6 shows a sectional view of an embodiment of the single use tip part 100 taken along the direction of the longitudinal axis 32 of the tip part 100, i.e. from its proximal end 33 to its distal end 34, with a side-wall therebetween. FIGS. 7-12 describe in more detail the structure of the housing in connection with light transmission and features to prevent light entering the imaging device. FIGS. 16-25B describe in further detail the structure of the instrument elevator and aspects of the housing related to the operation of the instrument elevator.

The tip part 100 comprises at least a first light emitting device 35, a second light emitting device 36, an camera 37 and a housing 38 encapsulating the light emitting devices 35, 36 and the camera 37 in a fluid tight manner. The light emitting devices may be referred to as light sources and may comprise light emitting diodes (LEDs). The housing 38 comprises a first housing part 39 with a first housing seat 40 and a second housing part 41 with a second housing seat 42. The first housing part 39 and the second housing part 41 fit together at their respective housing seats 40, 42 and are sealed along their common contact line at the housing seats 40, 42 forming a shell. On its proximal end 33 the first housing part 39 has an annular connection part 43/connection section 43 for (sealed) mechanical, electrical and/or hydraulic/pneumatic connection with/to the insertion tube 14.

In the present embodiment, the entire first housing part 39 as well as the entire second housing part 41 consist of a light transparent plastic/resin material and are made preferably by injection molding. In variations thereof, the portions of the side-wall through which light is emitted are transparent and other portions may be non-transparent. For example, the side-wall and the distal end may be transparent, and portions of the proximal end might be non-transparent. The housing parts may also be transparent to X-rays, by which it is meant that the housing parts are substantially invisible in X-ray images. By substantially invisible it is meant that tissue lying beneath the housing parts, in use, is visible in the X-ray images.

The first housing part 39 also comprises a socket-like first light guiding section 44 and a socket-like second light guiding section 45, each for guiding light being emitted by the light emitting devices 35, 36 to the outside of the tip part 100. The first light guiding section 44 comprises an (first) inside surface 46, while the second light guiding section 45 comprises an (second) inside surface 47. Both inside surfaces 46, 47 preferably are highly glossy to avoid transmission losses of light emitted by the light emitting devices 35, 36. Additionally, the first light guiding section 44 comprises an (first) outside surface 48, while the second light guiding section 45 comprises an (second) outside surface 49. Both outside surfaces 48, 49 are relatively rough compared to other outside surface areas of the housing 38 in order to distribute light exiting the tip part 100 from its inside to the outside. The roughness RA is provided by a sand blasting process and may be more than 1 μm, preferably between 1 μm and 10 μm, more preferred about 2.5 μm. The space/volume between the inside surfaces 46, 47 and the outside surfaces 48, 49 is filled with the transparent material of the housing 38.

The inside surfaces 46, 47 also serve for attachment/contacting of a first LED 35 as first light emitting device 35 and of a second LED 36 as second light emitting device 36. The first LED 35 and the second LED 36 each are attached to the concerning inside surface 46, 47 preferably by transparent glue 50. On the side opposite the transparent glue 50 the LEDs 35, 36 are connected to a printed circuit board (PCB) 51, which is located in a cavity 52 provided within the housing 38. Accordingly, the PCB is held by the socket-like light guiding sections 44, 45 via the LED's 35, 36. The PCB 51 is oriented essentially parallel to the longitudinal axis 32 of the tip such that light emitting directions of the LED's are substantially orthogonal to the longitudinal axis 32. In particular, the plane of the PCB 51 is arranged in an angle a of 4° to 10° to the longitudinal axis 32, preferred of 6° to the longitudinal axis 32.

Also arranged on the PCB 51 is the camera 37. The camera 37 comprises an imaging/camera chip 53 located on and electrically connected to/with the PCB 51 as well as a focusing system 54, in particular a lens system 54 for providing an image on the imaging chip 53. An optical axis 56 of the lens system 54 is, substantially, parallel to the optical axes 55 of light emitted by the LEDs 35, 36. Therefore, also, the camera 37 and the lens system 54 as well as its optical axis 56 are arranged orthogonal to the plane of the PCB 51 like the LED's 35, 36.

The lens system 54 comprises a stack of lenses 57 stacked in the direction of the optical axis 56 inside a so-called lens barrel, which is carried by the imaging/camera chip 53. Such a lens barrel—imaging chip—unit is well known in the prior art so that a detailed description is not needed here. The lens barrel is arranged within and surrounded by an opaque protective ring 58, which may comprise a cover, foil, or annular protrusion, which, in this example, is made by 2K molding with the transparent first housing part 39. Overmolding is also permissible. 2K molding comprises injection molding different materials in a 2k injection molding machine. Both processes are well known. Overmolding can achieve similar results but requires moving a part from one cavity to another, and is therefore more inefficient. On the other hand, a 2k injection molding machine requires more complex molds and is therefore requires a larger capital investment. Outside the protective ring 58 the first housing part 39 is provided with a circular opening (through hole) 65 designed to receive the protective ring 58 and the stack of lenses 57. The protective ring 58 also may serve for centering and adjusting the lens system 54. For this the ring 58 comprises a shoulder 59 providing an axial stop and an annular surface 60 for centering the distal end of the lens stack 57. The lens system 54 is arranged in a centered manner above (when related to the incoming light) the imaging chip 53, such that the image provided by the lens system 54 is projected onto the imaging chip 53, where it is transferred into image data, which are computed and/or stored by the PCB in a well-known manner.

To protect and shield light sensitive functional units of the tip part 100 as in particular the camera 37 with the imaging chip 53 and the lens system 54 from disturbing light which incidents into the transparent material of the housing 38, for example, from the outside and/or by the LED's 35, 36, at least parts of inner surfaces of the housing 38 facing the cavity 52 are covered/coated with an opaque coating 61. Additionally, or alternatively the imaging chip 53 is also shielded by an opaque potting 61 filled into the cavity 52. Further, a space between the stack of lenses 57 and the protective ring 58 may be filled/casted with additional opaque potting The tip part 100 further comprises a (cleaning) nozzle 62. As the nozzle 62 is located below (radial outside of) the first light emitting device 35—which means within the area to be illuminated—it is also made of a transparent plastic material. Further, the nozzle 62 is preferably attached to the first housing part 39 of the tip part 100 by a transparent grout 64, such that also the grout 64 does not negatively affect illumination by the first LED 35. Alternatively, the nozzle 62 and the housing may be provided integrally, that is molded with the housing. The transparent nozzle 62 is designed for rinsing the tip part 100, in particular an outer surface 63 of the camera 37. Further, the transparent nozzle 62 may be designed for insufflating a gas and/or air into a body cavity to be examined. Finally, in case of arranging a nozzle separate to the housing as described above, the (first) outside surface 48 has to be provided by the nozzle 62, itself.

As further is shown in FIGS. 7 to 12, an instrument elevator (so-called Albarran lever) 66 is pivoted in the first housing part 39. The instrument elevator 66 is located besides the opening 65 in the longitudinal direction on the same side of the first housing 39 and also coaxial to the working channel such that in a fully pivoted orientation of the instrument elevator 66 as shown in FIG. 10 a surgical instrument being shifted through the working channel is deflected by the instrument elevator into the same radial direction as the lens system 54 and substantially parallel to the optical axes 55 of the lens system 54. Further, it should be noted, that in FIGS. 7 to 12 the tip part 100 is shown without the PCB 51, the LEDs 35, 36 and the camera 37. Finally, it should be noted that the instrument elevator 66 is made of an opaque (resin) material thereby avoiding light reflections especially in case the instrument elevator is in fully pivoted orientation. The instrument elevator 66 functions and may be constructed substantially as the instrument elevator 200 described below. In some embodiments, the instrument elevator 66 is the instrument elevator 200 described below and the wire 30 is assembled with the instrument elevator 66 as described with reference to FIG. 26.

Figure 14:
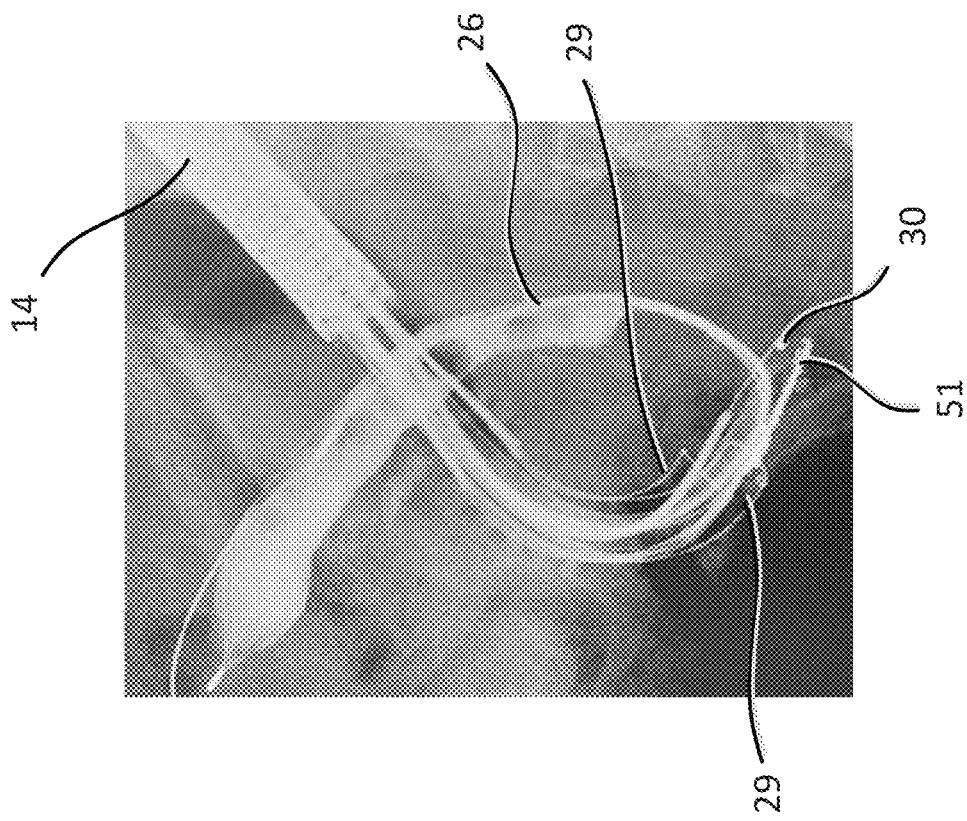
FIG. 14 is an X-ray image of the tip part illustrating the X-ray invisibility of the housing of the tip part.
Figure 13:
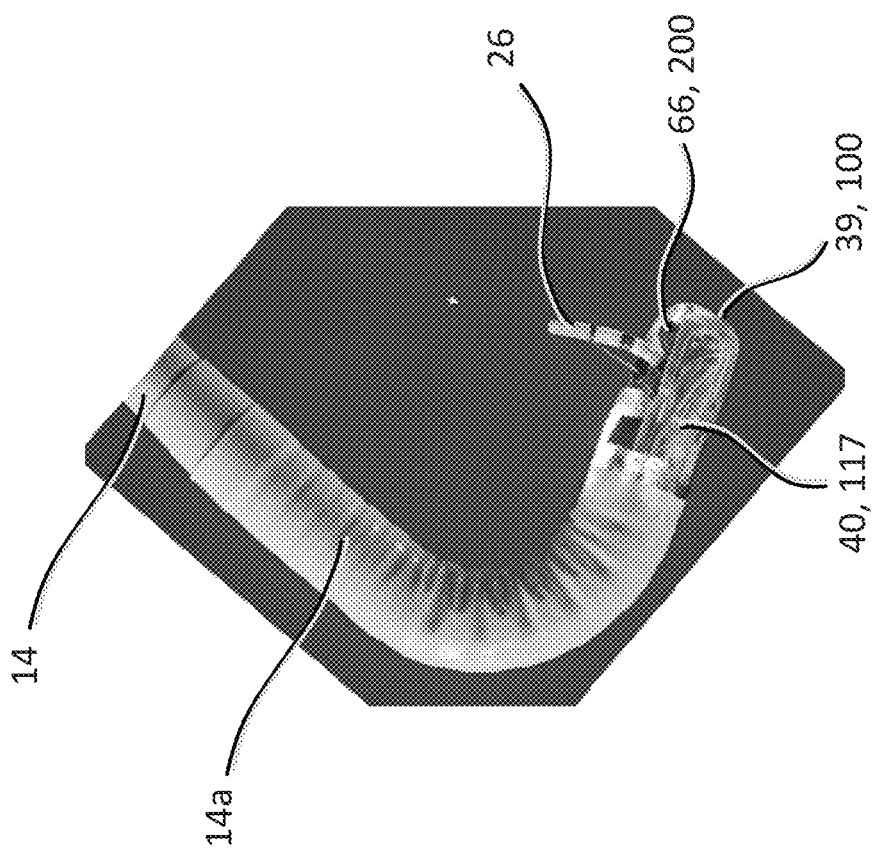
FIG. 13 is a photograph of a medical visualization device in which the housing of the tip part is X-ray transparent.

FIG. 13 is a photograph of the distal end of the medical visualization device showing the insertion tube 14, a sleeve 14a disposed over the bending section, the housing 39 of the tip part 100, the instrument elevator 66, 200, and the instrument 26. The photograph was taken against a black background. FIG. 14 is an X-ray image of the medical visualization device showing a metal coil of the insertion tube 14. In this example, the sleeve 14a, the bending section and the housing of the tip part, and the instrument elevator 66, 200 are invisible in the X-ray image. The steering wires 29, the circuit board 51, and the elevator wire 30 are visible in the X-ray image. It can be seen (into the paper) that tissue is also visible in the X-ray image which normally be covered by the tip part. Thus, making the tip part invisible to X-rays facilitates the procedure. But the inventors determined that it would be useful to see the instrument elevator, which would extend distally from the end of wire 30.

Figure 15:
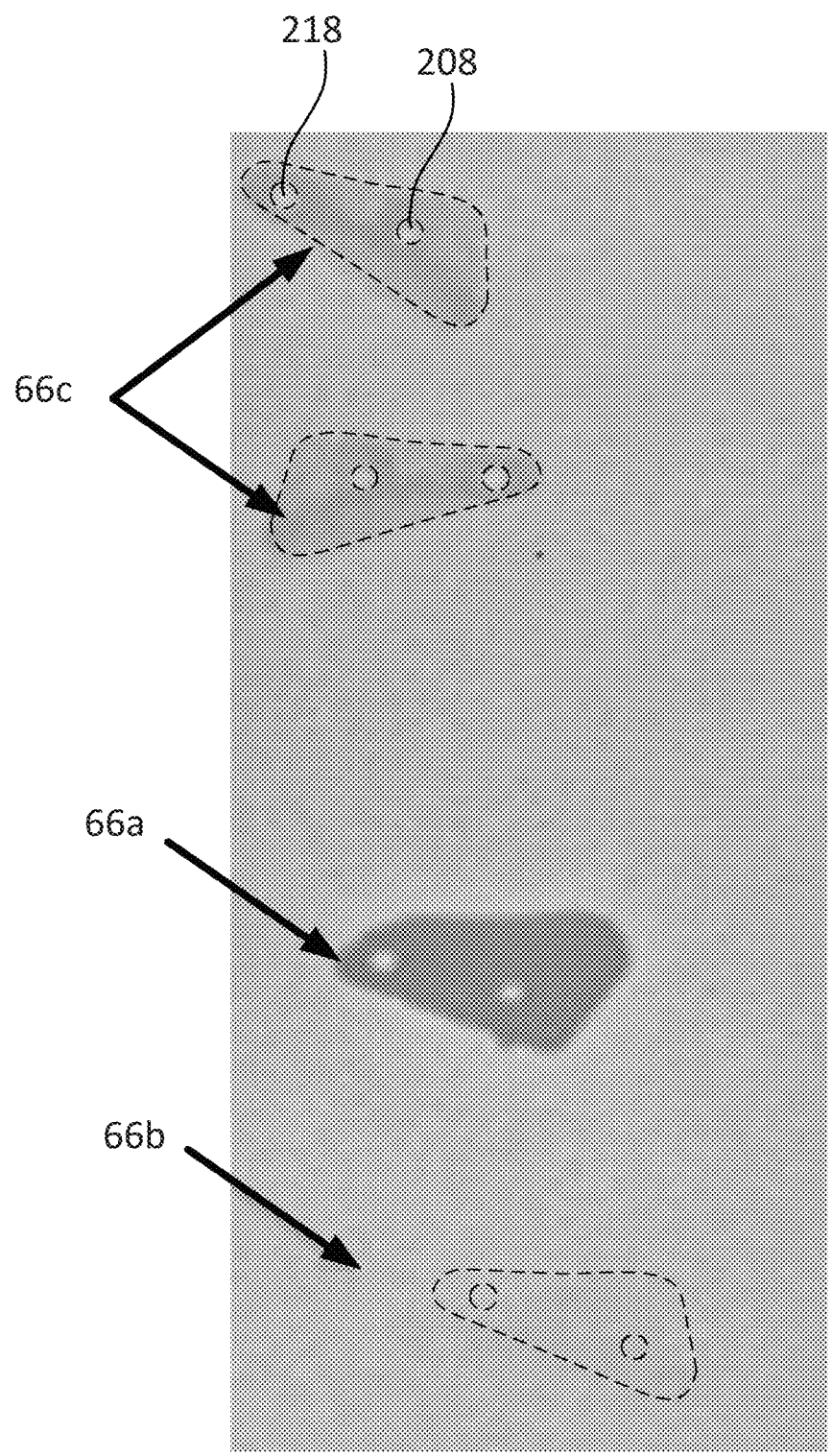
FIG. 15 is an X-ray image showing instrument elevators of various compositions, some of which are X-ray visible and one of which is X-ray invisible.

FIG. 15 is an X-ray image showing three instrument elevators. Instrument elevator 66a is metallic, instrument elevator 66b is made of a polymer similar or the same as the polymer used to make the housing and is therefore invisible in the X-ray image, and instrument elevator 66c comprises a polymer including a radiopacity agent and is therefore visible in the X-ray image. An example polymer for the transparent instrument elevator 66b is a medium density acetal homopolymer named Delrin(RM) SC655 NC010. An example polymer for the visible instrument elevator 66c is a medium density acetal homopolymer with a radiopacity agent, for example Dupont's Delrin® FG500MXD, and Ensinger's TECAPEEK MT XRO (PEEK), TECASON P MT XRO (PPSU) and TECAFORM® AH UD. Generally, medium density acetal homopolymers can be injection molded to make high precision parts. The opacity agent can comprise barium sulfate, for example.

Advantageously, an X-ray transparent housing with a radiopaque instrument elevator facilitates visualisation of the patient's tissue "beneath" the tip part while still providing position information based on the radiopaque nature of the instrument elevator.

The instrument elevator may comprise an X-ray detectable material, such as a radiopacity agent. For example, the instrument elevator may be made of a material, such as polyoxymethylene (POM), comprising a radiopacity agent. A radiopacity agent may be any agent capable of stopping or reducing passage of X-rays. Some exemplary radiopacity agents may be barium sulphate or titanium dioxide. However, any known radiopacity agent or X-ray detectable material may be used. A combination of a plurality of different radiopacity agents may be used. By providing the instrument elevator with an X-ray detectable material, the instrument elevator may be visible on an X-ray image of a patient during a procedure using the medical visualisation device. Thereby, an X-ray image may be used to guide and/or confirm the position and/or orientation of the instrument elevator inside the patient.

Polymer crystallinity may also be increased to make the instrument elevator more visible to X-rays. Crystallinity is increased by using linear polymers, decreasing the cooling rate during molding, and avoiding use of plasticizers. By contrast, the housing's crystallinity may be decreased by using highly branched polymers, increasing the cooling rate, and adding plasticizers. Furthermore, increasing the crystallinity of the instrument elevator relative to the housing also provides the instrument elevator with higher resistance to deformation. POM is an example of an intrinsically opaque polymer having high crystalline composition, in the order of 70-80%. Other polymers with crystallinity of 70% or higher may be used. Of course polymers with lower crystallinity can be used, particularly in compositions containing radiopacity agents and/or X-ray detectable materials.

The control wire 30 (see FIG. 3) is coupled to the instrument elevator 66 to adjust the guide angle. The control wire 30 may be connected to the control knob 28 (see FIG. 1), such that the operator may alter the guide angle of the instrument elevator 66 by operating the control knob 28 on the handle 12, which may have a designated dial or lever for operating the instrument elevator 66. The instrument elevator 66 may comprise a conduit 208 (see FIG. 22) and the control wire 30 may be coupled to the instrument elevator 66 by extending through the conduit 208. Furthermore, a sleeve element 140 (see FIG. 22) may be provided to further facilitate coupling of the control wire 30 to the instrument elevator 66. The conduit has a slightly larger diameter than the sleeve element 140.

Figure 21A:
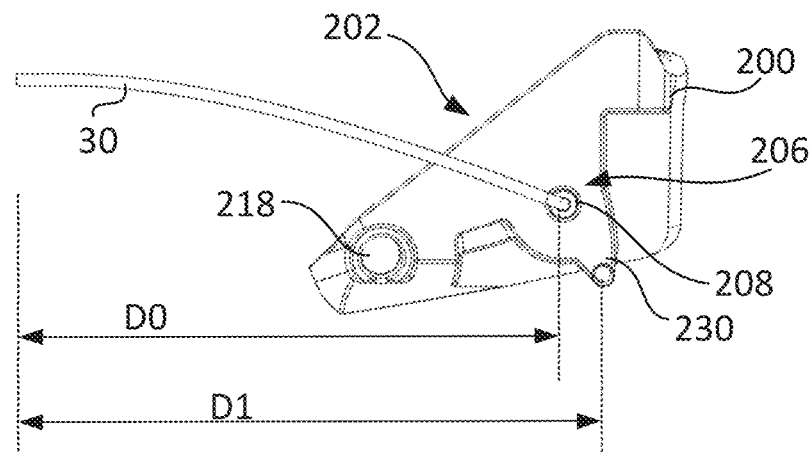
FIGS. 21A and 21B are perspective views of the instrument elevator of FIG. 18.
Figure 21B:
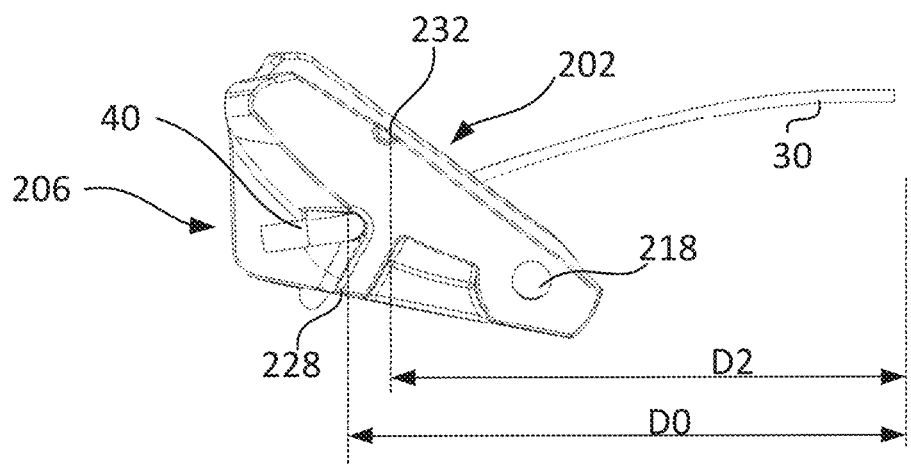
Figure 22:
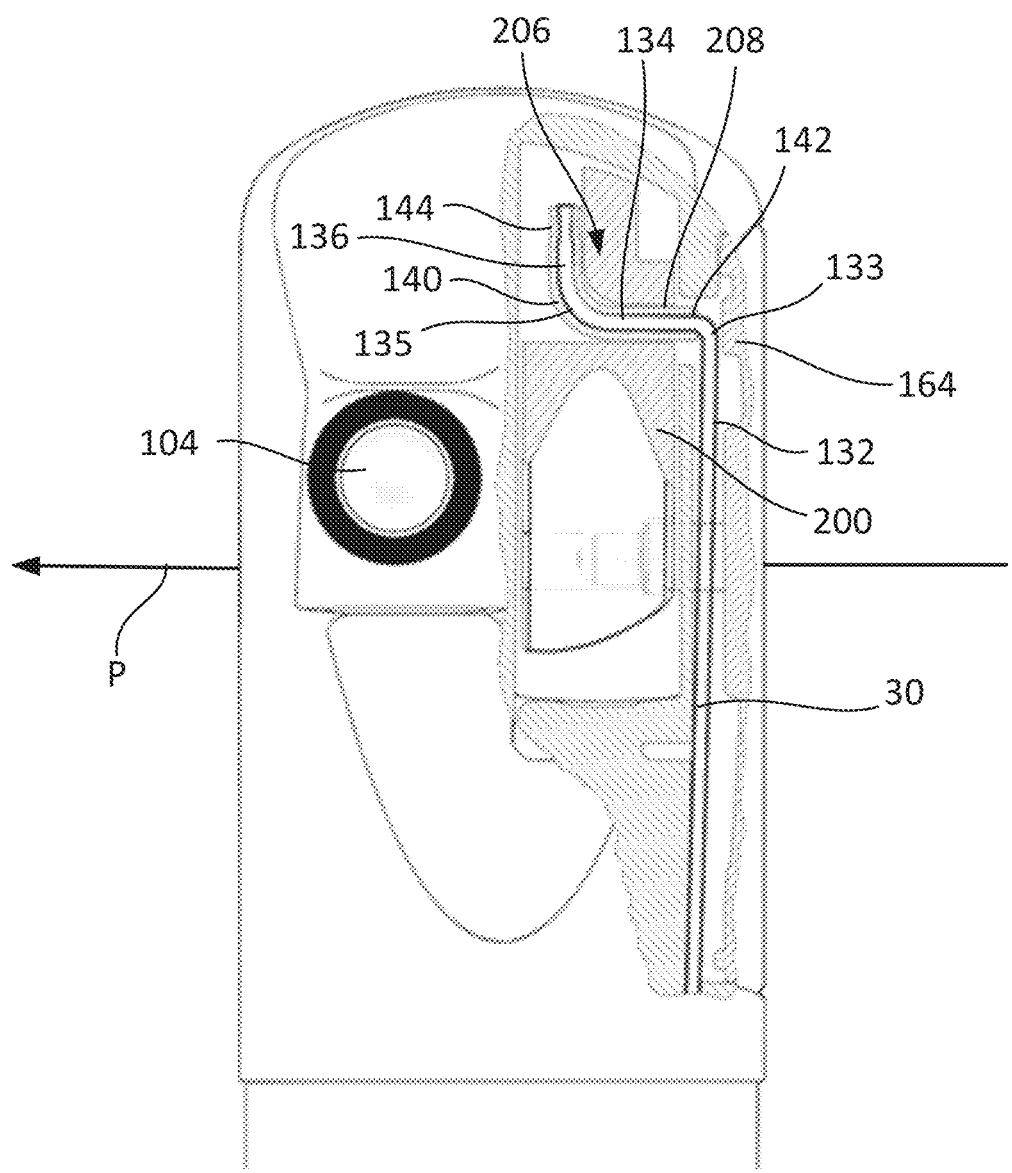
FIG. 22 is a sectional view of the tip part of FIG. 16.

As shown in FIG. 22, the control wire may have a primary segment 132, a secondary segment 134, and a tertiary segment 136, a first bend 133 between the primary segment 132 and the secondary segment 134, and a second bend 135 between the secondary segment 134 and the tertiary segment 136. The secondary segment 134 is between the primary segment 132 and the tertiary segment 136 and the secondary segment 134 extends through the conduit 208. The secondary segment 134 is parallel to the pivot axis P. The instrument elevator 66 may comprises support points configured to contact sidewalls of the tip part and disposed on opposite sides of the instrument elevator 66. Example support points are described with reference to FIGS. 21A and 21B, where the location of the support points is also described. Additional details of the coupling of the control wire to the instrument elevator are provided with reference to FIGS. 22 and 23A-24B.

The assembly of the endoscope tip part 100 for a single use duodenum endoscope is described as follows:

To begin with, the PCB 51 already carrying the LED's 35, 36 and the camera 37 including the imaging/camera chip 53 and the lens barrel is attached to the first housing part 39 at socket-like connecting portions representing the first and second light guiding sections 44, 45 preferably by a glue layer. In this mounting/connecting position, the lens barrel penetrates the through opening within the first housing part 39 to be uncovered to the outside wherein the opaque protective ring 58 forms a light blocking layer between the lens barrel and the first housing part 39.

In a following step, the light transparent nozzle 62 is connected with the first housing part 39 thereby forming a further light guiding part/section of the light emitting path below the one LED 35, wherein an outer surface of the nozzle 62 provides the first outer light emitting outside surface 48 of the respective light emitting path.

After the second housing part 41 is fluid tightly connected to the first housing part 39 at the respective housing seats 40, 42, cavities inside the housing 38 are filled with the opaque material surrounding at least the lens barrel, the LED's 35, 36 (including the contact area (glue layer) between the LED's 35, 36 and the first housing part 39), as well as the socket-like first and second light guiding sections 44, 45, thereby blocking light transmission through the housing 38, except the first and second outside surfaces 48, 49 at the first housing part 39 (and the nozzle 62).

Figure 16:
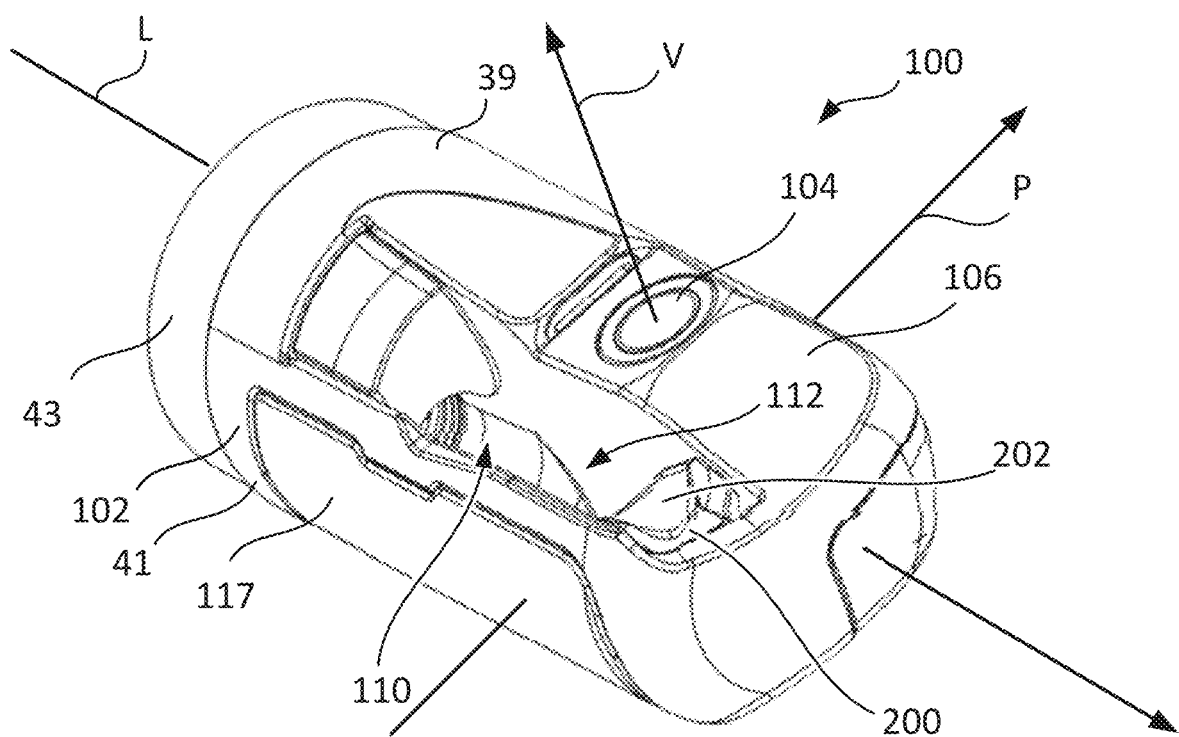
FIG. 16 is a perspective view of another embodiment of a tip part.
Figure 17:
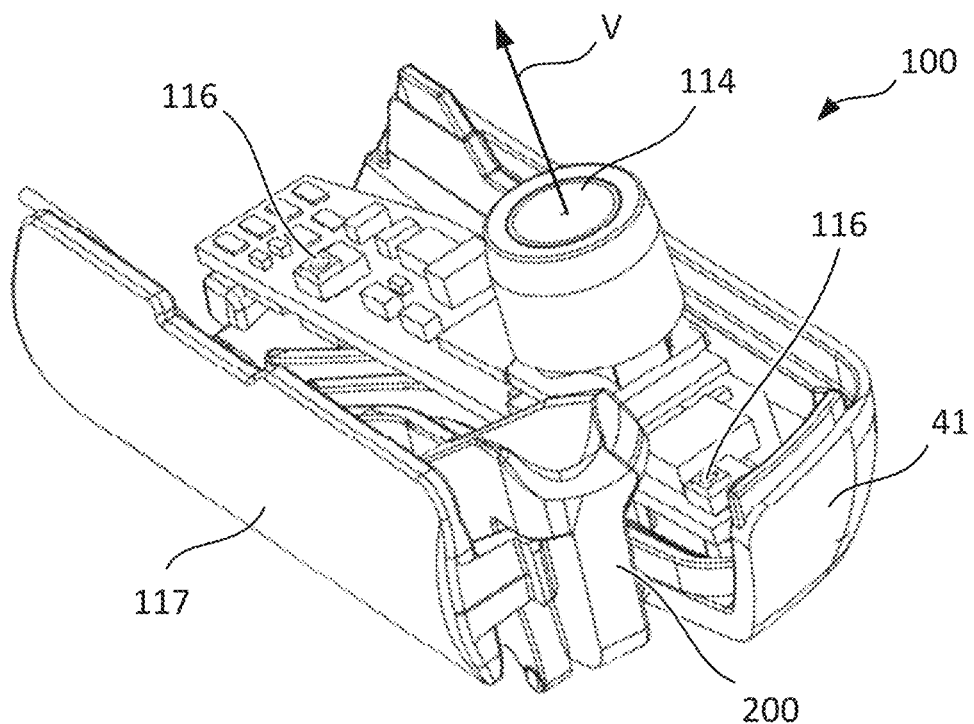
FIG. 17 is a partial perspective view of the tip part of FIG. 16.

FIG. 16 is a schematic diagram illustrating another embodiment of the tip part 100. The tip part 100 has a tip part housing 102. The tip part 100 and/or the tip part housing 102 extends from the distal tube end 18 (see FIG. 1) along a longitudinal axis L. The housing 102 may comprise the first housing part 39 and the second housing part 41, described with reference to FIG. 6, and on its proximal end the annular connection part 43. Preferably, at least the first housing part and the second housing part are transparent. FIG. 17 illustrates the housing seat 42 of the first housing part 39.

The tip part 100 comprises a window portion 104, e.g. forming part of a side wall 106 of the tip part housing 102. The window portion 104 allows a view from the interior of the tip part housing 102 in a viewing direction V. The viewing direction V is substantially perpendicular to the longitudinal axis L. For example, the tip part may comprise a camera (see FIG. 4), arranged to look through the window portion 104 in the viewing direction V.

The tip part 100 comprises a tip part instrument channel 110 with an instrument opening 112 defined by the tip part housing 102. The tip part instrument channel 110 is configured to be coupled with the first channel 20 of the insertion tube 14 (see FIGS. 1 and 3), thereby allowing an instrument being inserted through the first channel 20, e.g. via the instrument port 19, to protrude through the tip part instrument channel 110 and distally out through the instrument opening 112.

The tip part 100 comprises an instrument elevator 200 configured for directing an instrument being inserted through the first channel in a desired direction. The instrument elevator 200 has a guide surface 202 for engaging with an instrument protruding through the tip part instrument channel 110. The instrument elevator 200 is described in more detail below. The instrument elevator 200 is pivotable around a pivot axis P to adjust a guide angle between the guide surface 202 and the longitudinal axis L. The pivot axis P is substantially perpendicular to the longitudinal axis L and substantially perpendicular to the viewing direction V.

The control wire 30 (see FIG. 3) is coupled to the instrument elevator 200 to transfer a force exerted on the control wire 30 to the instrument elevator 200 to adjust the guide angle. The control wire 30 may be connected to the control knob 28 (see FIG. 1), such that the operator may alter the guide angle of the instrument elevator 200 by operating the control knob 28 on the handle 12, which may have a designated dial or lever for operating the instrument elevator 200.

The tip part 100 comprises a sidewall element 117 covering a control wire compartment.

FIG. 17 is a perspective view illustrating the exemplary tip part 100 of FIG. 16 with part of the housing removed. As seen, the tip part 100 comprises a camera 114 arranged to look in the viewing direction V, e.g. through the window portion as explained above. The camera 114 may be the same as camera 37 and may be mounted to the circuit board and housing in the same manner. Also, the tip part 100 comprises one or more light sources 116, in the illustrated example two light sources 116, for providing illumination in the viewing direction V. The light sources 116 may be the same as the light emitting devices 35 and 36 and may be mounted to the circuit board, adhered to the housing, and oriented in the same manner. One or more electrical conductors 24 (see FIG. 3) may be provided to transmit a camera signal indicative of image data generated by the camera 114 through the insertion tube 14. Similarly, the one or more electrical conductors 24 may provide power to the light sources 116 to increase or decrease illumination.

Figure 18:
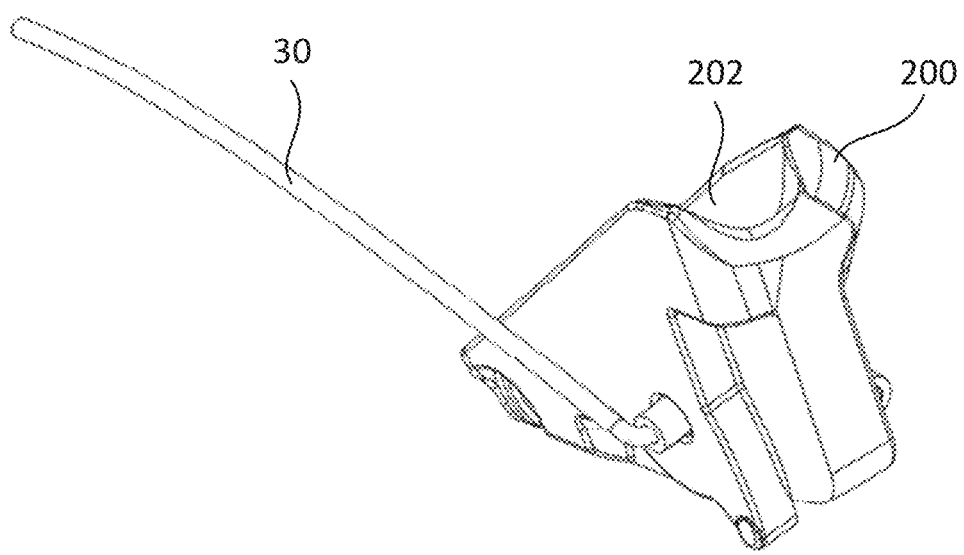
FIG. 18 is a perspective view of an embodiment of an instrument elevator of the tip part of FIG. 16 also showing an exemplary connected control wire.

FIG. 18 is a perspective view illustrating the exemplary instrument elevator 200 with the control wire 30 being connected, such that pulling the control wire 30 results in the instrument elevator 200 being raised and pushing the control wire 30 results in the instrument elevator 200 being lowered. Hence, the guide angle may be increased or decreased. Utilizing a solid wire may promote better ability to lower the instrument elevator 200 by pushing the control wire 30, as a solid wire has less tendency to buckle upon compression.

Figure 19A:
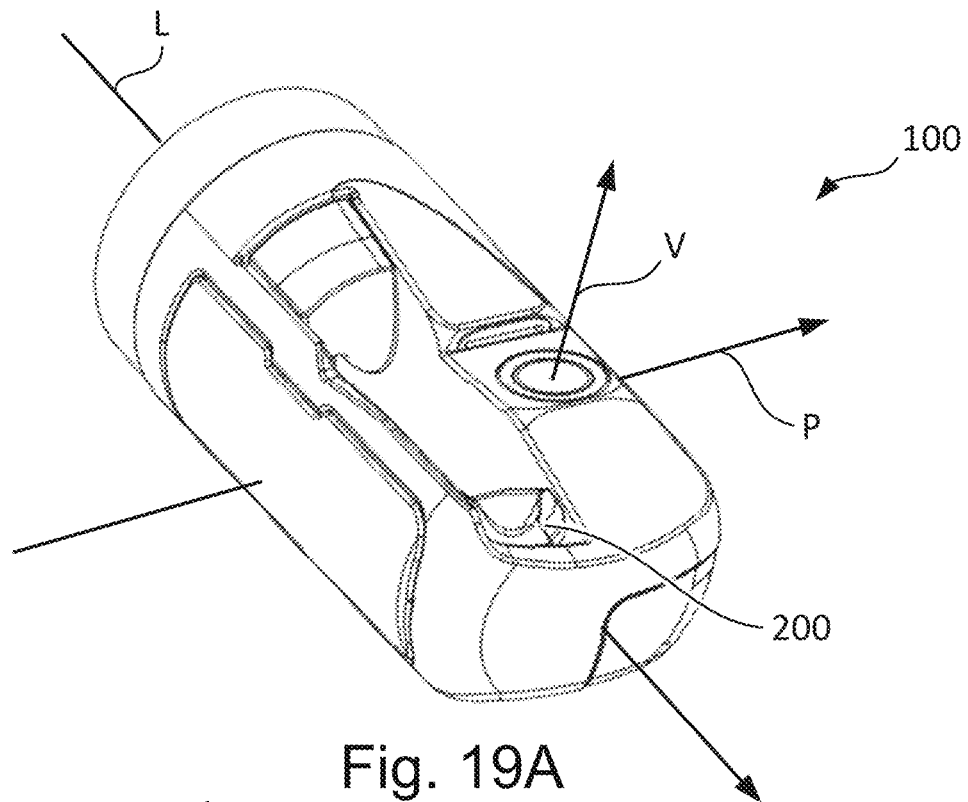
FIGS. 19A and 19B are perspective views of the tip part of FIG. 16. showing a position of the instrument elevator of FIG. 18.
Figure 19B:
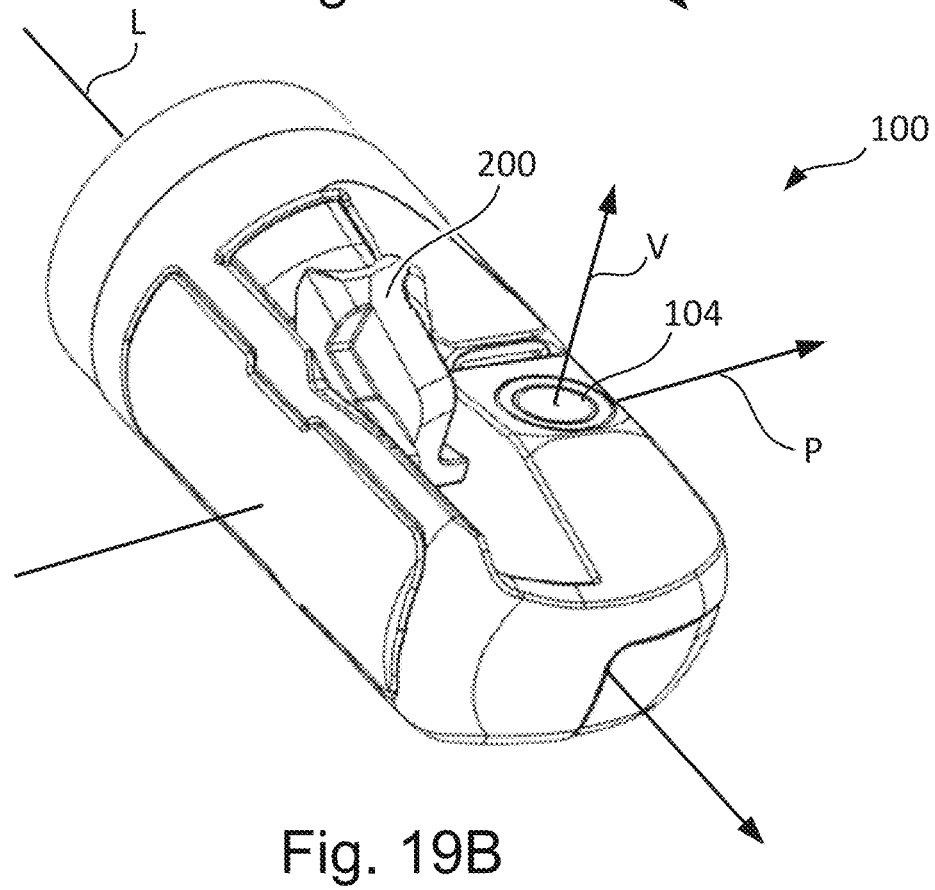

FIGS. 19A and 19B schematically illustrates the tip part 100 as described with respect to the previous figures, with the instrument elevator 200 being in a lowered position in FIG. 19A and in a raised position in FIG. 19B.

As seen in FIG. 19B, in the raised position (and in other positions between the lowered position and the raised position), the instrument elevator 200 may be within the field of view of the camera and/or may be in a position where light is reflected from the instrument elevator 200 and affects the image captured through the window portion 104, a dark surface may cause shadows and a bright surface may cause overexposure. Therefore, it may be advantageous to provide the instrument elevator in a colour which balances the reflected light, such as a grey colour e.g. a colour with L* between 15 to 75, a* between negative 10 to positive 10, and b* between negative 10 to positive 10, as measured by a CIEL*a*b* colour code system.

Figure 20A:
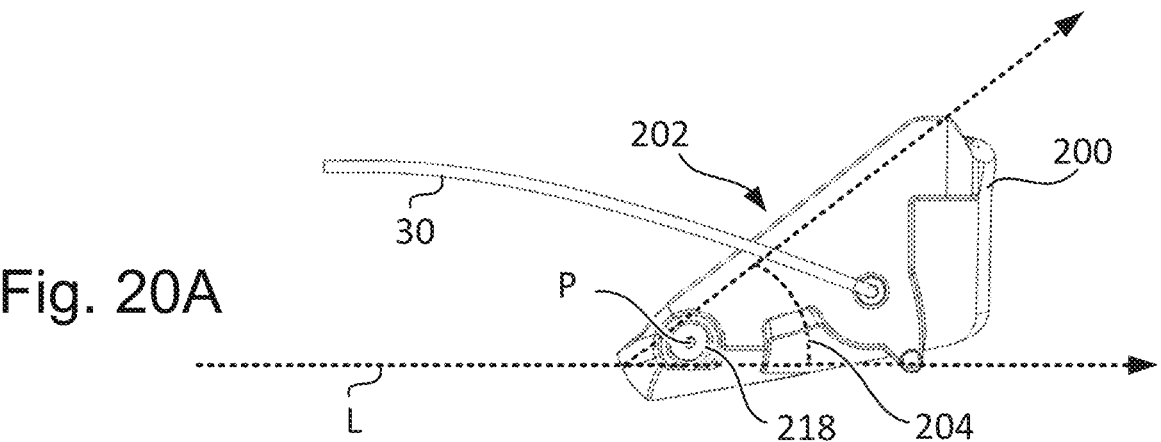
FIGS. 20A-20C are side views of the instrument elevator of FIG. 18 in different positions relative to a longitudinal axis of the tip part.
Figure 20B:
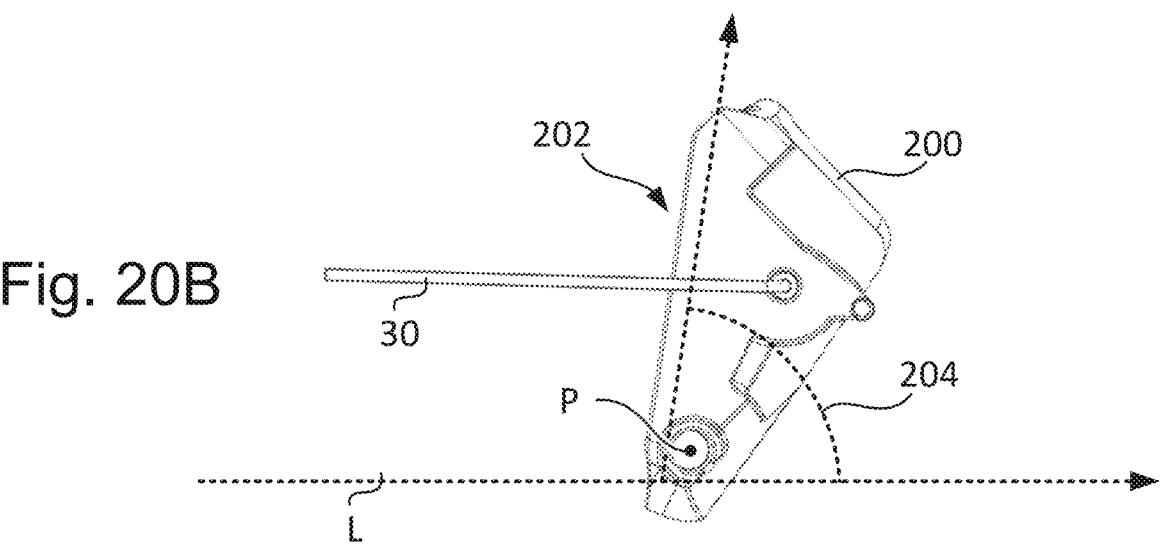
Figure 20C:
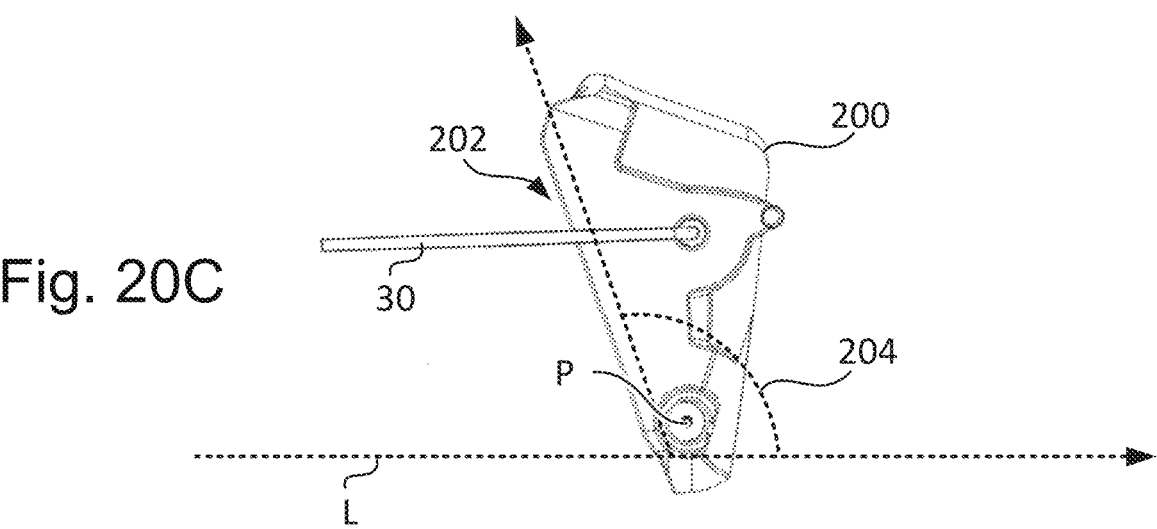

FIGS. 20A-20C are side views illustrating the instrument elevator 200 being in different positions with a varying guide angle 204 between the guide surface 202 and the longitudinal axis L. In FIG. 20A, the instrument elevator 200 is in a lowered position. In FIG. 20B, the instrument elevator 200 is in an intermediate position, wherein the guide angle 204 is bigger than in the lowered position. In FIG. 20C, the instrument elevator 200 is in a raised position, wherein the guide angle 204 is bigger than in the intermediate position. For example, the guide angle 204 may be 40 degrees in the lowered position, 85 degrees in the intermediate position, and 120 degrees in the raised position.

As illustrated, the instrument elevator 200 pivots around a pivot axis P. More particularly, an axle may extend through the axle opening 218, to allow rotation of the instrument elevator 200.

FIGS. 21A and 21B are side views illustrating the instrument elevator 200 with the control wire 30, as described above, from opposite sides.

The instrument elevator 200 comprises a coupling part 206 for coupling the control wire 30 to the instrument elevator 200, such as to allow the control wire to raise and lower the instrument elevator. The coupling part 206 has a conduit 208. The control wire 30 is coupled to the instrument elevator 200 by extending through the conduit 208. Furthermore, a sleeve element 140 may be provided to further facilitate coupling of the control wire 30 to the instrument elevator 200.

Upon raising the instrument elevator 200, by pulling the control wire 30, the control wire 30 and the sleeve element 140 is allowed to rotate inside the conduit 208. Thus, the conduit has a slightly larger diameter than the sleeve element 140.

Because the control wire 30 is positioned on a first side of the instrument elevator 200, operating the instrument elevator 200 by pushing or pulling the control wire will introduce a twisting moment of the instrument elevator 200. To maintain position of the instrument elevator 200 in the tip housing, the instrument elevator comprises support points configured to contact sidewalls of the tip part. The instrument elevator 200 comprises a first support point 230 on the first side of the instrument elevator 200 (indicated in FIG. 21A) and second support point 232 on the second side of the instrument elevator 200 (indicated in FIG. 21B). As shown, the first support point 230 is on a first side of the instrument elevator 200 and the second support point 232 is on an opposite, second, side of the instrument elevator 200. The first and second sides are perpendicular to the axle with the second support point 232 outward from a line traversing the axle opening 218 and the conduit 208 and thus adjacent to the guide surface 202, and the first support point 230 is inward from said line.

Figure 23A:
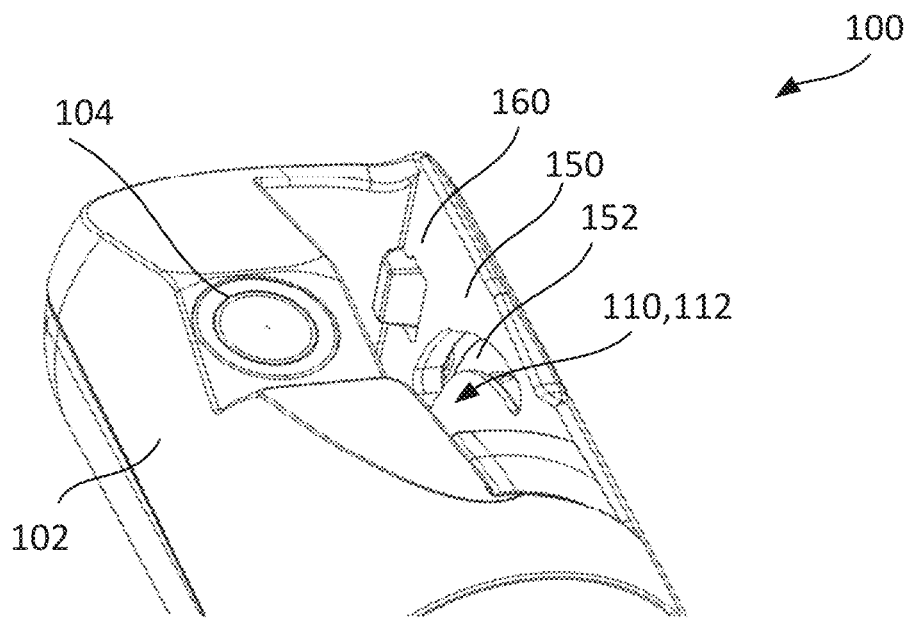
FIGS. 23A and 23B are perspective views of the tip part of FIG. 16 with the instrument elevator removed.

The first support point 230 is arranged to contact a first sidewall 160 of the tip part instrument channel 110 (see FIG. 23A). The second support point 232 is arranged to contact a second sidewall 162 of the tip part instrument channel 110 (see FIG. 23B).

A distance D1 between the distal tube end and the first support point 230 is larger than a distance D0 between the distal tube end and the conduit 208 of the instrument elevator 200. A distance D2 between the distal tube end and the second support point 232 is smaller than the distance D0 between the distal tube end and the conduit 208 of the instrument elevator 200. Thereby, the first support point 230 and the second support point 232 counteracts the twisting moment of the instrument elevator 200 induced by the force applied by the control wire 30. In particular, the distances as illustrated is advantageous for counteracting the twisting moment induced by pulling the control wire. As shown, distances D0, D1 and D2 are measured with the instrument elevator 200 in the down position, as shown in FIG. 20A.

FIG. 22 is a sectional view of the tip part 100, as described with respect to the previous figures, showing the instrument elevator 200 in cross section, to allow illustration of elements enclosed therein. In coupling the control wire 30 to the instrument elevator 200, it is desired that pulling the control wire 30 does not result in the control wire being pulled off the instrument elevator 200.

To couple the control wire 30 to the instrument elevator 200, the control wire has a primary segment 132 and a secondary segment 134. The control wire 30 further comprising a first bend 133 between the primary segment 132 and the secondary segment 134. The primary segment 132 is arranged on a first side of the coupling part 206 along the pivot axis P and the secondary segment 134 extends through the conduit 208 of the coupling part 206. The first bend 133 may be about 90 degrees, as illustrated, or may be more than 90 degrees, i.e. bent more than illustrated, or may be less than 90 degrees, i.e. bent less than illustrated. The secondary segment 134 is parallel to the pivot axis P.

In the illustrated example, the control wire 30 further has a tertiary segment 136. The secondary segment 134 is between the primary segment 132 and the tertiary segment 136. The control wire 30 further comprises a second bend 135 between the secondary segment 134 and the tertiary segment 136. The tertiary segment 136 may be arranged on a second side of the coupling part 206, as seen in FIG. 21B. The second side may be opposite the first side of the coupling part 206 along the pivot axis P. The second bend 135 may be about 90 degrees, as illustrated, or may be more than 90 degrees, i.e. bent more than 90 degrees as illustrated, or may be less than 90 degrees, i.e. bent less than 90 degrees as illustrated. As illustrated, the primary segment 132 and the tertiary segment 136 may be substantially parallel. In some exemplary embodiments, the second bend 135 is more than 90 degrees, e.g. such as to curl around the coupling part 206 of the instrument elevator.

A housing inner side wall 164 prevents the control wire 30, such as the secondary segment 134 of the control wire 30, from being pulled out of the conduit 208 and maintain attachment of the control wire 30 to the instrument elevator 200, during pulling on the control wire.

A sleeve element 140 may be provided. The sleeve element 140 may further facilitate coupling of the control wire 30 to the instrument elevator 200. In the illustrated example, the sleeve element 140 encloses the secondary segment 134, the tertiary segment 136 and the second bend 135 of the control wire 30. In other exemplary embodiments, the sleeve element 140 may comprise one or more of the secondary segments 134, the tertiary segment 136 and the second bend 135. The sleeve element may be secured to the secondary segment 134 by compression of a first portion 142 of the sleeve element 140 enclosing a portion of the secondary segment 134. Alternatively or additionally, the sleeve element 140 may be secured to the tertiary segment 136 by compression of a second portion 144 of the sleeve element 140 enclosing a portion of the tertiary segment 136. The sleeve element 140 may be a polymeric tube, preferably a polymeric tube of transparent polymer.

The sleeve element 140 and the control wire 30 may be bent concurrently, i.e. the sleeve element 140 may be bent with the control wire 30, during forming of the second bend 135, such that the sleeve element 140 encloses the second bend 135 of the control wire 30.

The sleeve element 140 may provide increased stiffness to the control wire 30. Thereby, the control wire is further restricted from being pulled out of the conduit 208, because of the inability to bend around the corners at the first bend 133, i.e. between the conduit 208 and the housing inner side wall 164, and at the second bend 135.

Figure 23B:
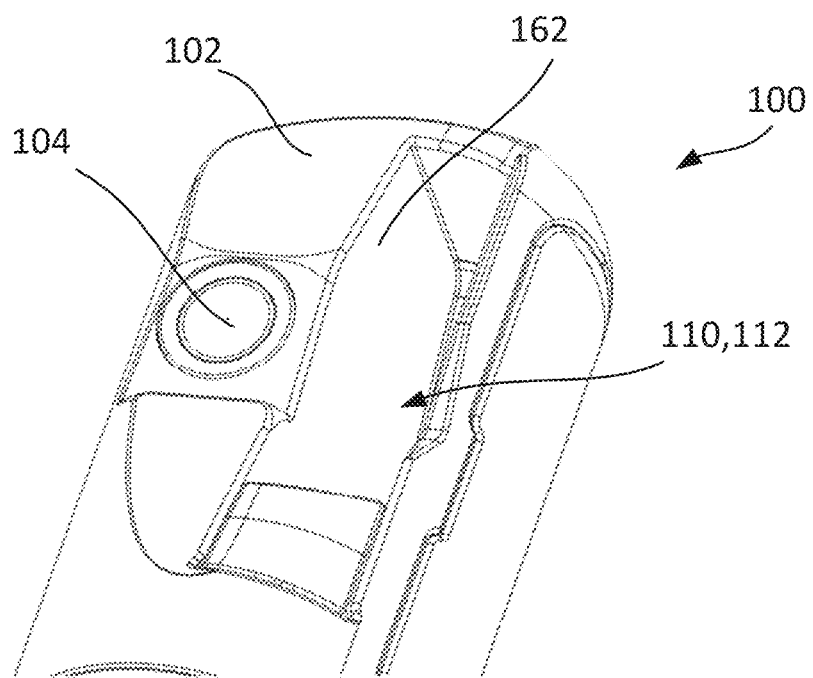

FIGS. 23A and 23B are perspective views of the exemplary tip part 100 with the instrument elevator removed to allow a view of the tip part instrument channel 110 and instrument opening 112. The tip part instrument channel comprises a first sidewall 160 (FIG. 23A) and a second sidewall 162 (FIG. 23B) opposite the first sidewall 160. The first sidewall 160 is a first side of an intermediate wall 150 separating the tip part instrument channel 110 and a control wire compartment 154 (see FIG. 24A). The intermediate wall 150 further defines an intermediate wall opening 152 between the tip part instrument channel 110 and the control wire compartment, allowing the control wire to extend from the control wire compartment to tip part instrument channel where it is coupled to the instrument elevator.

Figure 24A:
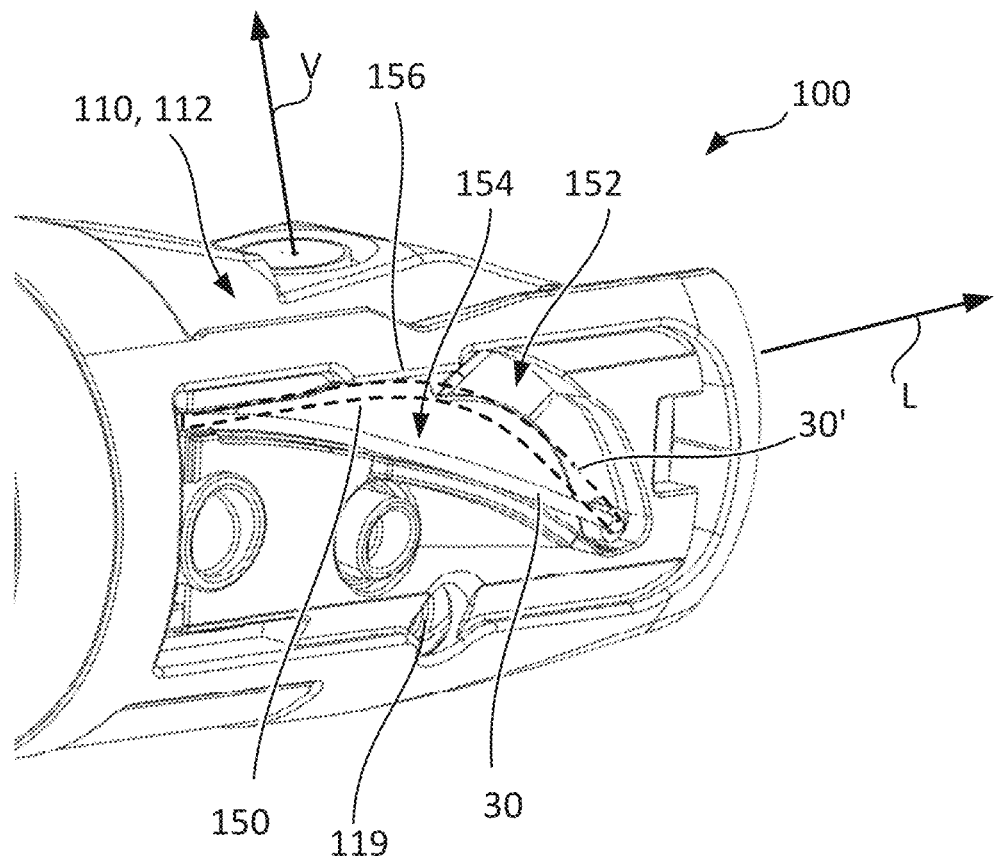
FIG. 24A is another perspective view of the tip part of FIG. 16.
Figure 24B:
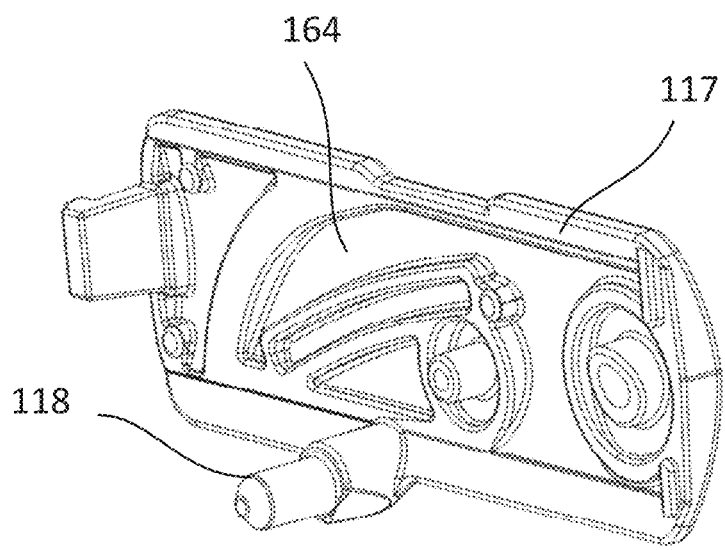
FIG. 24B is a perspective view of a portion of the housing of the tip part of FIG. 16.

FIG. 24A is a perspective view of the exemplary tip part 100 with the sidewall element 117 removed to allow a view of the control wire compartment 154. The exemplary sidewall element 117 is illustrated in FIG. 24B.

The tip part comprises the intermediate wall 150 separating the tip part instrument channel 110 and the control wire compartment 154. The control wire compartment 154 is coupled with the second channel of the insertion tube, such that the control wire 30 being arranged in the second channel may extend into the control wire compartment 154.

The intermediate wall 150 defines the intermediate wall opening 152 between the tip part instrument channel 110 and the control wire compartment 154. The control wire 30 extends through the control wire compartment 154 and through the intermediate wall opening 152 to the instrument elevator in the tip part instrument channel 110. The intermediate wall opening is arc shaped or semi-circular shaped to allow movement of the control wire 30 in accordance with a change of position of the instrument elevator, i.e. from the lowered position to the raised position.

The control wire compartment 154 comprises a ceiling surface 156. The ceiling surface 156 is between the distal tube end and the intermediate wall opening 152 along the longitudinal axis L. The ceiling surface 156 is configured for engagement with the control wire 30 to limit deflection of the control wire 30 in the viewing direction V, as illustrated by the dashed line illustrating a control wire 30' being pushed. The ceiling surface 156 thereby transfers a pushing force exerted on the control wire 30, 30' to the instrument elevator to minimize the guide angle. In this way, the operator has the possibility to completely lower the instrument elevator. Furthermore, the ceiling surface 156 may facilitate assembly of the tip part 100, as the contact of the control wire 30 against the ceiling surface 156 aids in pushing the instrument elevator down into place. Assembly of the tip part 100 is explained in further details below with reference to FIG. 26.

As seen in FIG. 24B, the tip part comprises an axle 118, which extends along the pivot axis when inserted through an axle opening 119 of the tip part housing 102 and an axle opening 218 of the instrument elevator (see FIG. 21A). As illustrated, the axle 118 may be provided on the sidewall element 117. Thereby, the axle 118 may be inserted upon closing the control wire compartment 154 with the sidewall element 117. Also, the housing inner side wall 134 may be provided by the sidewall element 117. The housing inner side wall prevents the control wire 30 from being pulled out of the conduit 208 and retain the control wire 30 attached to the instrument elevator 200 (see FIG. 22).

Figure 25A:
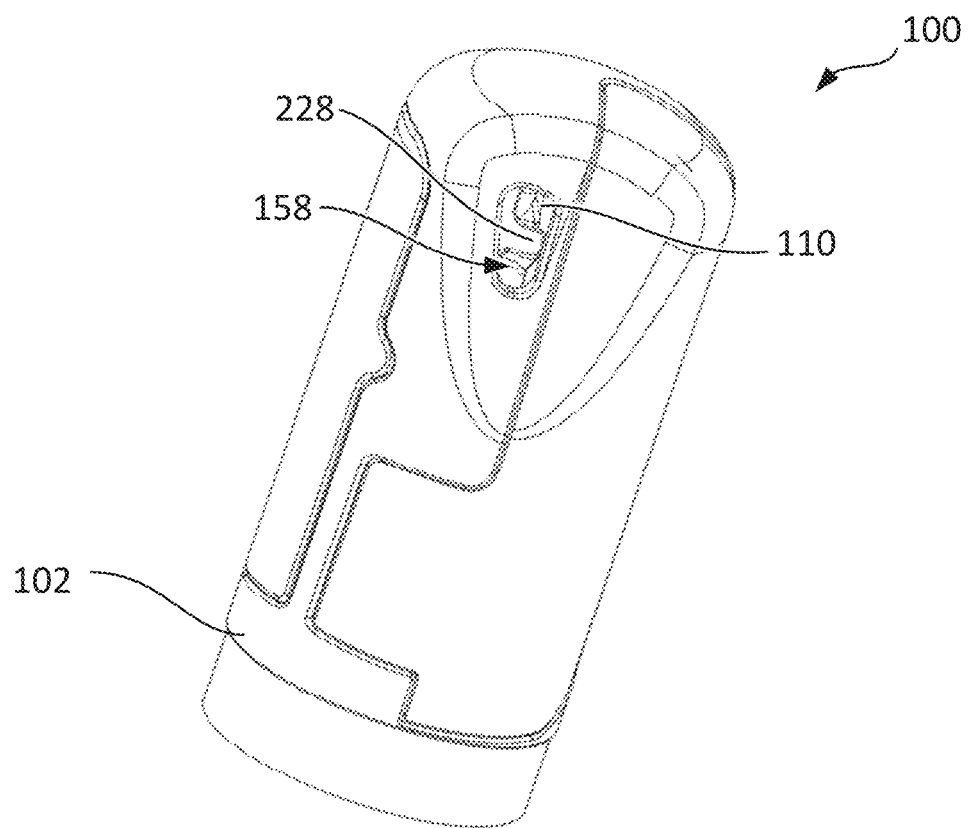
FIG. 25A is a perspective bottom view of the tip part.
Figure 25B:
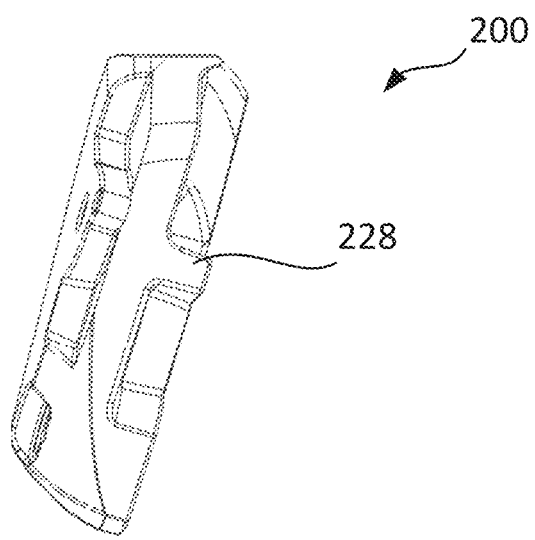
FIG. 25B is a perspective bottom view of the instrument elevator.

FIGS. 25A and 25B are perspective views illustrating, respectively, the bottom of the exemplary tip part 100 and the instrument elevator 200.

As seen in FIG. 25A, the tip part housing 102 comprises a secondary opening 158 between the tip part instrument channel 110 and the exterior of the tip part housing 102. The secondary opening 158 is provided opposite the instrument opening 112 (see previous figures). As seen in FIG. 25B, the instrument elevator 200 comprises a protruding wall 228 opposite the guide surface 202 (see previous figures). The protruding wall 228 blocks part of the secondary opening 158, as seen in FIG. 25A, when the instrument elevator is in a lowered position. The protruding wall 228 has a surface area smaller than the area of the secondary opening 158.

The small surface area of the protruding wall, e.g. smaller than 1 mm$^2$, may facilitate breaking of, e.g., gallstones having entered into the housing. The secondary opening 158 allows fragments to be pushed out of the housing, to ensure that the instrument elevator 200 is not prevented from being positioned in the lowered position.

Figure 26:
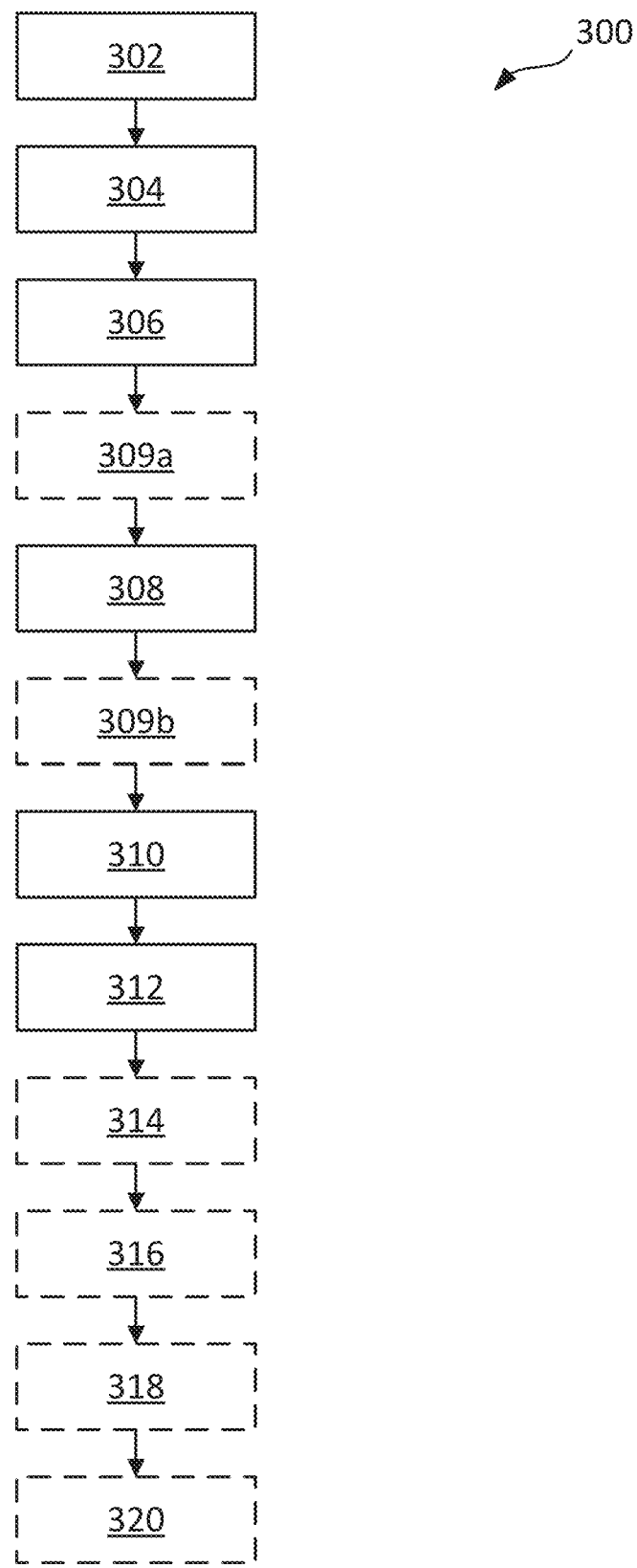
FIG. 26 is a block diagram of an embodiment of a method of assembly of a medical visualization device.

FIG. 26 is a block diagram of an exemplary method 300, such as a method 300 for assembly of a medical visualisation device, such as the medical visualisation device 100 as described with respect of the previous figures.

The method 300 comprises: providing 302 a tip part housing, such as the tip part housing 102 as described above; providing 304 an instrument elevator having a guide surface, such as the instrument elevator 200 as described above; providing 306 a control wire extending from a proximal end to a distal end, such as the control wire 30 as described above. The control wire comprises a distal portion extending to the distal end of the control wire.

The method 300 further comprises coupling 308 the distal portion of the control wire to the instrument elevator.

Coupling 308 the distal portion of the control wire to the instrument elevator may comprise inserting the control wire through a conduit of a coupling part of the instrument elevator, such that a primary segment of the control wire is arranged on a first side of the coupling part and a secondary segment of the control wire is extending through the conduit. The secondary segment forms part of the distal portion of the control wire. The control wire may be inserted through the conduit of the instrument elevator such that a tertiary segment of the control wire is arranged on a second side of the instrument elevator. The tertiary segment may form part of the distal portion of the control wire.

Coupling 308 the distal portion of the control wire to the instrument elevator may comprise bending the control wire to obtain a first bend between the primary segment and the secondary segment. Coupling 308 the distal portion of the control wire to the instrument elevator may comprise bending the control wire to obtain a second bend between the tertiary segment and the secondary segment.

Coupling 308 the distal portion of the control wire to the instrument elevator may comprise securing a sleeve element to the distal portion of the control wire such that the distal portion of the control wire is enclosed by the sleeve element.

Securing the sleeve element to the distal portion of the control wire may comprise compressing a portion of the sleeve element enclosing at least a portion of the distal portion of the control wire. The sleeve element may be secured to the distal portion of the control wire prior to bending the control wire to obtain the second bend. In this situation bending the control wire to obtain the second may include concurrently bending the sleeve element and the control wire to obtain the second bend.

After coupling 308 the distal portion of the control wire to the instrument elevator, the method comprises passing 310 the control wire through the instrument opening of the tip part housing in a proximal direction.

The tip part housing may comprise an intermediate wall separating the tip part instrument channel and a control wire compartment (see, e.g., FIG. 24A). The intermediate wall defines an intermediate wall opening between the tip part instrument channel and the control wire compartment. Furthermore, the control wire compartment is couplable to a second channel of the medical visualisation device. Thus, passing 310 the control wire through the instrument opening of the tip part housing may include passing the control wire through the intermediate wall opening and through the control wire compartment. The control wire may further be passed through the second channel of the medical visualisation device.

The method 300 may comprise threading 309a the proximal end of the control wire through the instrument opening of the tip part housing in a proximal direction after coupling 308 the distal portion of the control wire to the instrument elevator. Alternatively, the control wire extends through the second channel of the medical visualisation device prior to coupling 308 the distal portion of the control wire to the instrument elevator. In such situation the method 300 may comprise threading 309b the distal end of the control wire through the instrument opening of the tip part housing in a distal direction prior to coupling 308 the distal portion of the control wire to the instrument elevator.

The method 300 further comprises, e.g. after having passed 310 the control wire through the instrument opening in a proximal direction, inserting 312 the instrument elevator together with the distal portion of the control wire through the instrument opening of the tip part housing, such as to position the instrument elevator in a seat for the instrument elevator in the tip part instrument channel. Upon insertion 312 into the seat, the instrument elevator may snap into place after which it is retained by the tip part housing. As explained above with reference to FIG. 24A, the ceiling surface 156 may facilitate the insertion 312 of the instrument elevator by as the contact of the control wire 30 against the ceiling surface 156 aids in pushing the instrument elevator downwards, such as to snap it into place.

The method 300 may further comprise inserting 316 an axle through an axle opening of the instrument elevator, and optionally through one or more axle opening of the tip part housing. A sidewall element comprising the axle may be provided, and attaching the sidewall element to the tip part housing may include inserting 316 the axle.

The method 300 may comprise, e.g. prior to inserting 316 the axle, aligning 314 the axle opening of the instrument elevator with an axle opening of the tip part housing. Thus inserting 316 the axle may comprise inserting the axle through the axle opening of the tip part housing and the axle opening of the instrument elevator.

The method 300 may comprise providing 318 a handle and an insertion tube extending from the handle to a distal tube end, the insertion tube comprising the second channel, and the method may comprise attaching 320 the tip part housing to the distal tube end of the insertion tube.

Exemplary embodiments of the present disclosure are set out in the following exemplary items:

Item 1. A medical visualisation device comprising a handle and an insertion tube extending from the handle to a distal tube end, the insertion tube comprising a first channel, a second channel, and a control wire extending through the second channel, the medical visualisation device comprising a tip part at the distal tube end, the tip part having a tip part housing extending from the distal tube end along a longitudinal axis, the tip part comprising:

a window portion allowing a view from the interior of the tip part housing in a viewing direction being substantially perpendicular to the longitudinal axis;

a tip part instrument channel with an instrument opening defined by the tip part housing, the tip part instrument channel being coupled with the first channel of the insertion tube allowing an instrument being inserted through the first channel to protrude through the tip part instrument channel and distally out through the instrument opening;

an instrument elevator having a guide surface for engagement with the instrument protruding through the tip part instrument channel, the instrument elevator being pivotable around a pivot axis to adjust a guide angle between the guide surface and the longitudinal axis, the pivot axis being substantially perpendicular to the longitudinal axis and the viewing direction, the control wire being coupled to the instrument elevator to transfer a force exerted on the control wire to the instrument elevator to adjust the guide angle.

Item 2. Medical visualisation device according to item 1, wherein the control wire has a primary segment and a secondary segment, the control wire further comprising a first bend between the primary segment and the secondary segment, the instrument elevator comprising a coupling part having a conduit, the primary segment being arranged on a first side of the coupling part along the pivot axis and the secondary segment extending through the conduit.

Item 3. Medical visualisation device according to item 2, wherein the first bend is between 80-100 degrees, such as between 85-95 degrees, such as 90 degrees.

Item 4. Medical visualisation device according to any of items 2-3, wherein the first bend has a minimum radius of curvature between 0.1-0.5 mm.

Item 5. Medical visualisation device according to any of items 2-4, wherein the control wire has a tertiary segment, wherein the secondary segment is between the primary segment and the tertiary segment, the control wire further comprising a second bend between the secondary segment and the tertiary segment, the tertiary segment being arranged on a second side of the coupling part, the second side being opposite the first side of the coupling part along the pivot axis.

Item 6. Medical visualisation device according to item 5, wherein the second bend is between 80-100 degrees, such as between 85-95 degrees, such as 90 degrees.

Item 7. Medical visualisation device according to any of items 5-6, wherein the second bend has a radius of curvature between 0.2-1.5 mm.

Item 8. Medical visualisation device according to any of items 5-6, wherein the primary segment and the tertiary segment are substantially parallel.

Item 9. Medical visualisation device according to any of items 2-8, wherein the tip part comprises a sleeve element enclosing the secondary segment and/or the tertiary segment.

Item 10. Medical visualisation device according to item 9, wherein the sleeve element is secured to the secondary segment by compression of a first portion of the sleeve element enclosing at least a portion of the secondary segment.

Item 11. Medical visualisation device according to any of items 9-10, wherein the sleeve element is secured to the tertiary segment by compression of a second portion of the sleeve element enclosing at least a portion of the tertiary segment.

Item 12. Medical visualisation device according to any of items 9-11, wherein the sleeve element has been bent with the control wire during forming of the second bend, such that the sleeve element encloses the second bend.

Item 13. Medical visualisation device according to any of the preceding items, wherein the control wire is a solid wire.

Item 14. Medical visualisation device according to any of the preceding items, wherein the control wire is a high strength steel wire.

Item 15. Medical visualisation device according to any of the preceding items, wherein the instrument elevator is made of polyoxymethylene (POM).

Item 16. Medical visualisation device according to any of the preceding items, wherein the instrument elevator has an elevator colour, the elevator colour being a grey colour, e.g. a colour with L* between 15 to 75, a* between negative 10 to positive 10, and b* between negative 10 to positive 10, as measured by a CIEL*a*b* colour code system.

Item 17. Medical visualisation device according to any of the preceding items, wherein the instrument elevator comprises an X-ray detectable material.

Item 18. Medical visualisation device according to any of the preceding items, wherein the tip part comprises an axle extending along the pivot axis and through an axle opening of the instrument elevator.

Item 19. Medical visualisation device according to any of the preceding items, wherein the tip part comprises an intermediate wall separating the tip part instrument channel and a control wire compartment, the control wire compartment being coupled with the second channel of the insertion tube, the intermediate wall defines an intermediate wall opening between the tip part instrument channel and the control wire compartment, and wherein the control wire extends through the control wire compartment and through the intermediate wall opening to the instrument elevator in the tip part instrument channel.

Item 20. Medical visualisation device according to item 19, wherein the control wire compartment comprises a ceiling surface between the distal tube end and the intermediate wall opening along the longitudinal axis, the ceiling surface being configured for engagement with the control wire to limit deflection of the control wire in the viewing direction, and to transfer a pushing force exerted on the control wire to the instrument elevator to minimize the guide angle.

Item 21. Medical visualisation device according to any of the preceding items, wherein the tip part housing comprises a secondary opening between the tip part instrument channel and the exterior of the tip part housing, the secondary opening being provided opposite the instrument opening, wherein the instrument elevator comprises a protruding wall opposite the guide surface, and wherein the protruding wall blocks part of the secondary opening when the instrument elevator is in a lowered position, the protruding wall comprises a surface area smaller than the area of the secondary opening.

Item 22. Medical visualisation device according to item 21, wherein the surface area of the protruding wall is smaller than 1 mm$^2$, such as smaller than 0.50 mm$^2$, such as smaller than 0.4 mm$^2$.

Item 23. Medical visualisation device according to any of the preceding items, wherein the instrument elevator comprises a first support point on the first side of the instrument elevator along the pivot axis, the first support point is arranged to contact a first sidewall of the tip part instrument channel, and wherein a distance between the distal tube end and the first support point is larger than a distance between the distal tube end and the conduit of the instrument elevator.

Item 24. Medical visualisation device according to any of the preceding items, wherein the instrument elevator comprises a second support point on the second side of the instrument elevator along the pivot axis, the second support point is arranged to contact a second sidewall of the tip part instrument channel, wherein a distance between the distal tube end and the second support point is smaller than a distance between the distal tube end and the conduit of the instrument elevator, wherein, optionally, a window portion allowing a view from the interior of the tip part housing in a viewing direction being substantially perpendicular to the longitudinal axis.

Item 25. Medical visualisation device according to any of the preceding items, wherein the tip part housing is transparent to X-ray.

Item 26. Method for assembly of a medical visualisation device comprising:

providing a tip part housing extending along a longitudinal axis and comprising a window portion forming part of a side wall of the tip part housing and allowing a view from the interior of the tip part housing in a viewing direction being substantially perpendicular to the longitudinal axis, the tip part housing defining an instrument opening of a tip part instrument channel, wherein the tip part instrument channel is couplable to a first channel of the medical visualisation device;

providing an instrument elevator having a guide surface adapted for engagement with the instrument being inserted through the first channel to protrude through the tip part instrument channel and distally out through the instrument opening;

providing a control wire extending from a proximal end to a distal end, the control wire comprising a distal portion extending to the distal end;

coupling the distal portion of the control wire to the instrument elevator;

after coupling the distal portion of the control wire to the instrument elevator passing the control wire through the instrument opening of the tip part housing in a proximal direction;

inserting the instrument elevator together with the distal portion of the control wire through the instrument opening of the tip part housing to position the instrument elevator in a seat for the instrument elevator in the tip part instrument channel.

Item 27. Method according to item 26, wherein the instrument elevator, upon insertion into the seat, snaps into place and is retained by the tip part housing.

Item 28. Method according to any of items 26-27 comprising inserting an axle through an axle opening of the instrument elevator.

Item 29. Method according to item 28, comprising aligning the axle opening of the instrument elevator with an axle opening of the tip part housing, and wherein the axle is inserted through the axle opening of the tip part housing and the axle opening of the instrument elevator.

Item 30. Method according to any of items 26-29 comprising providing a sidewall element comprising the axle, and wherein the method comprises attaching the sidewall element to the tip part housing and attaching the sidewall element includes inserting the axle through the axle opening of the instrument elevator and optionally through the axle opening of the tip part housing.

Item 31. Method according to any of items 26-30, wherein the tip part housing comprises an intermediate wall separating the tip part instrument channel and a control wire compartment, the intermediate wall defining an intermediate wall opening between the tip part instrument channel and the control wire compartment, the control wire compartment is couplable to a second channel of the medical visualisation device, and wherein passing the control wire through the instrument opening of the tip part housing includes passing the control wire through the intermediate wall opening and through the control wire compartment.

Item 32. Method according to any of items 26-31 comprising providing a handle and an insertion tube extending from the handle to a distal tube end, the insertion tube comprising the first channel and the second channel, the method comprising attaching the tip part housing to the distal tube end.

Item 33. Method according to any of items 26-32 wherein coupling the distal portion of the control wire to the instrument elevator comprises inserting the control wire through a conduit of a coupling part of the instrument elevator, such that a primary segment of the control wire is arranged on a first side of the coupling part and a secondary segment of the control wire is extending through the conduit, the secondary segment forming part of the distal portion of the control wire.

Item 34. Method according to item 33 wherein coupling the distal portion of the control wire to the instrument elevator comprises bending the control wire to obtain a first bend between the primary segment and the secondary segment.

Item 35. Method according to any of items 33-34 wherein the control wire is inserted through the conduit of the instrument elevator such that a tertiary segment of the control wire is arranged on a second side of the instrument elevator, the tertiary segment forming part of the distal portion of the control wire, and wherein coupling the distal portion of the control wire to the instrument elevator comprises bending the control wire to obtain a second bend between the tertiary segment and the secondary segment.

Item 36. Method according to any of items 26-35, wherein coupling the distal portion of the control wire to the instrument elevator comprises securing a sleeve element to the distal portion of the control wire such that the distal portion of the control wire is enclosed by the sleeve element.

Item 37. Method according to item 36, wherein securing the sleeve element to the distal portion of the control wire comprises compressing a portion of the sleeve element enclosing at least a portion of the distal portion of the control wire.

Item 38. Method according to any of items 36-37 as dependent on item 34, wherein the sleeve element is secured to the distal portion of the control wire prior to bending the control wire to obtain the second bend, and wherein bending the control wire to obtain the second bend includes concurrently bending the sleeve element and the control wire to obtain the second bend.

Item 39. Method according to any of items 26-38 wherein the control wire extends through the second channel of the medical visualisation device prior to coupling the distal portion of the control wire to the instrument elevator, and wherein the method comprises threading the distal end of the control wire through the instrument opening of the tip part housing in a distal direction prior to coupling the distal portion of the control wire to the instrument elevator.

Item 40. Method according to any of items 26-38 comprising threading the proximal end of the control wire through the instrument opening of the tip part housing in a proximal direction after coupling the distal portion of the control wire to the instrument elevator.

Item 41. Tip part for or of a single use endoscope, in particular for or of a single use duodenoscope, the tip part comprising at least one light emitting device, an imaging device, also referred to as a camera, and a housing encapsulating the at least one light emitting device and the imaging device in a fluid tight manner, wherein the at least one light emitting device is arranged on a planar printed circuit board provided within the housing, and wherein the housing, at least in part, is made from a transparent material, in particular a transparent plastic material, preferably by injection molding, and comprises at least one transparent light guiding part or light guiding section for guiding light emitted by the at least one light emitting device to an outside of the tip part.

Item 42. Tip part according to claim 41, wherein the at least one light emitting device comprises a LED.

Item 43. Tip part according to claim 41 or 42, wherein the imaging device is arranged on and/or connected to the printed circuit board, which is oriented essentially parallel to a longitudinal axis of the tip part extending from a distal tip end to a proximal tip end, in particular in an angle a of 4° to 10° to the longitudinal axis, most preferred of 6° to the longitudinal axis.

Item 44. Tip part according to claim 43, wherein the at least one light emitting device are arranged on and the imaging device are arranged on and/or connected to a common printed circuit board.

Item 45. Tip part according to one of items 41 to 44, wherein the at least one light emitting device is connected to the housing by transparent adhesive, preferably such that there is no direct contact between the at least one light emitting device and the housing.

Item 46. Tip part according to one of items 41 to 45, wherein, an inside surface of the light guiding part or light guiding section of the housing is highly glossy and/or is covered by a light transparent glue at a contact area between the light guiding part and the light emitting device to prevent or avoid transmission losses of light emitted by the at least one light emitting device.

Item 47. Tip part according to one of items 41 to 46, wherein an outside surface of the light guiding parts or the light guiding sections of the housing is designed as a rough surface with a roughness RA of more than 1 pm, preferably with a roughness RA between 1 µm and 10 µm, more preferred with a roughness RA of about 2.5 µm.

Item 48. Tip part according to one of items 41 to 47, wherein the imaging device comprises an imaging chip provided by the printed circuit board and a focusing system, in particular a lens system for providing an image on the imaging chip.

Item 49. Tip part according to one of items 41 to 48, wherein the tip part comprises an opaque layer, in particular an opaque potting, provided for shielding disturbing light entering the transparent housing, which opaque potting in particular shields the imaging chip and the focusing system.

Item 50. Tip part according to one of items 41 to 49, wherein the focusing system is surrounded by an opaque protective ring, which preferably is made by 2K molding with the transparent housing.

Item 51. Tip part according to one of items 41 to 50, wherein the optical axis of light emitted from the tip part is essentially parallel to the optical axis of the imaging device.

Item 52. Tip part according to one of items 41 to 51, wherein the tip part further comprises a transparent nozzle device for rinsing the tip part, in particular an outer surface of the imaging device and/or for insufflating a gas and/or air, wherein the transparent nozzle device preferably is attached to the tip part by a transparent grout.

Item 53. Endoscope, preferable duodenoscope, comprising an endoscope shaft being adapted to be inserted into a hollow organ of a patient, and comprising a tip part according to one of items 41 to 52 which is provided at a distal end portion of the endoscope shaft.

Item 54. A method for manufacturing a tip of a single-use endoscope, in particular for manufacturing a tip of a single-use duodenoscope, according to one of the claims 41 to 53, further comprising inserting, in particular along a straight direction, a planar printed circuit board having at least one light emitting device arranged thereon and an imaging device, preferably arranged thereon and/or connected thereto, within an at least in part transparent, preferably a complete transparent, housing of the tip part; preferably connecting and/or attaching the at least one light emitting device to a light guiding section of the housing by a transparent adhesive, preferably by a glue layer; and encapsulating the planar printed circuit board, the least one light emitting device and the imaging device in a fluid tight manner in the housing, preferably by fluid tightly connecting a second housing part to a first housing part.

Item 55. The method according to item 54, wherein the method further comprises filling opaque potting in a cavity surrounding at least a focusing system of the imaging device, preferably further surrounding a contact area between the at least one light emitting device and/or the light guiding section.

The disclosure has been described with reference to a preferred embodiment. However, the scope of the invention is not limited to the illustrated embodiment, and alterations and modifications can be carried out without deviating from the scope of the invention.

Throughout the description, the use of the terms "first", "second", "third", "fourth", "primary", "secondary", "tertiary" etc. does not imply any particular order or importance but are included to identify individual elements. Furthermore, the labelling of a first element does not imply the presence of a second element and vice versa.

LIST OF REFERENCES 2 visualisation system
4 monitor device
6 monitor connector
8 display
10 medical visualisation device
11 device connector
12 handle
14 insertion tube
16 proximal tube end
18 distal tube end
19 instrument port
20 first channel
22 second channel
24 electrical conductors
28 control knob
30 control wire
132 primary segment
133 first bend
134 secondary segment
135 second bend
136 tertiary segment
140 sleeve element
142 first portion of sleeve element
144 second portion of sleeve element
100 tip part
102 tip part housing
104 window portion
106 side wall
110 tip part instrument channel
112 instrument opening
114 camera
116 light source
117 sidewall element
118 axle
119 axle opening
150 intermediate wall
152 intermediate wall opening
154 control wire compartment
156 ceiling surface
158 secondary opening
160 first sidewall of tip part instrument channel
162 second sidewall of tip part instrument channel
164 housing inner side wall
200 instrument elevator
202 guide surface
204 guide angle
206 coupling part
208 conduit
218 axle opening
228 protruding wall
230 first support point
232 second support point
300 method
302 providing tip part housing
304 providing instrument elevator
306 providing control wire
308 coupling control wire to instrument elevator
309a threading control wire through instrument opening
309b threading control wire through instrument opening
310 passing control wire through instrument opening
312 inserting instrument elevator
314 aligning axle openings
316 inserting axle
318 providing handle and insertion tube
320 attaching tip part housing
L longitudinal axis
V viewing direction
P pivot axis

What is claimed is:
1. A medical visualization device comprising:
an insertion tube;
a tip part extending distally from the insertion tube, the tip part including a housing, an instrument elevator rotatably supported by the housing, a light emitting device having an optical axis, and a camera having a field of view; and a control wire extending through the insertion tube to the instrument elevator, wherein translation of the control wire causes the instrument elevator to rotate, wherein the housing is transparent in X-ray images and comprises an instrument opening and a secondary opening opposite the instrument opening;

wherein the camera is positioned within the housing;

wherein the light emitting device is positioned within the housing with the optical axis aimed to illuminate at least a portion of the field of view of the camera;

wherein the instrument elevator comprises a radiopacity agent; and wherein the instrument elevator comprises at least 70% polyoxymethylene (POM).

2. The medical visualization device of claim 1, wherein the housing comprises at least one light guiding section, and wherein the optical axis is aimed at the at least one light guiding section.

3. The medical visualization device of claim 2, wherein the light emitting device is adhered to the at least one light guiding section by transparent adhesive.

4. The medical visualization device of claim 1, wherein the housing defines an interior space, further comprising, in the interior space, opaque potting material surrounding the camera.

5. The medical visualization device of claim 4, wherein the opaque potting material is transparent in X-ray images.

6. The medical visualization device of claim 1, further comprising an opaque protective ring secured to the housing and defining a camera opening, and wherein the camera is at least partly positioned within the camera opening of the opaque protective ring.

7. The medical visualization device of claim 1, wherein the insertion tube comprises a bending section at a distal end thereof, the bending section being transparent in X-ray images.

8. The medical visualization device of claim 1, wherein the instrument elevator comprises an X-ray detectable material.

9. The medical visualization device of claim 1, wherein the instrument elevator has a color, and wherein the color comprises an L* between 15 to 75, an a* between negative 10 to positive 10, and a b* between negative 10 to positive 10, as measured by a CIEL*a*b* colour code system.

10. The medical visualization device of claim 1, wherein the housing comprises at least one light guiding section, wherein the optical axis is aimed at the at least one light guiding section, wherein the light emitting device is adhered to the at least one light guiding section by transparent adhesive, and wherein the housing defines an interior space, the medical visualization device further comprising,:

in the interior space, opaque potting material transparent in X-ray images and surrounding the camera,; and an opaque protective ring secured to the housing and defining a camera opening, and wherein the camera is at least partly positioned within the camera opening of the opaque protective ring.

11. The medical visualization device of claim 1, wherein the control wire has a primary segment, a secondary segment, and a first bend between the primary segment and the secondary segment, wherein the instrument elevator comprises a first side, a second side opposite the first side, and a conduit extending between the first side and the second side, and wherein the primary segment is arranged on the first side and the secondary segment extends through the conduit.

12. The medical visualization device of claim 11, wherein the control wire has a tertiary segment and a second bend between the secondary segment and the tertiary segment, and wherein the tertiary segment is positioned on the second side.

13. The medical visualization device of claim 12, further comprising a sleeve element enclosing the tertiary segment, the second bend and at least a portion of the secondary segment.

14. The medical visualization device of claim 1, wherein the tip part comprises an intermediate wall separating an instrument channel and a control wire compartment, the intermediate wall having an intermediate wall opening, and wherein the control wire extends through the control wire compartment and through the intermediate wall opening to the instrument elevator.

15. The medical visualization device of claim 14, wherein the control wire compartment comprises a ceiling surface to limit deflection of the control wire in a viewing direction.

16. The medical visualization device of claim 14, wherein the instrument elevator comprises a first side, a second side opposite the first side, and a conduit extending between the first side and the second side, wherein the instrument elevator comprises a first support point on the first side and a second support point on the second side, the second support point offset relative to the first support point.

17. The medical visualization device of claim 1, further comprising a handle, wherein the insertion tube extends from the handle.

18. A visualization system comprising the medical visualization device of claim 1 and a monitor device, wherein the monitor device can be communicatively coupled with the medical visualization device to present live images on a display based on images obtained by the medical visualization device.

19. The visualization system of claim 18, wherein the monitor device comprises the display.

20. A medical visualization device comprising:

an insertion tube;

a tip part extending distally from the insertion tube, the tip part including a housing, an instrument elevator rotatably supported by the housing, a light emitting device having an optical axis, and a camera having a field of view; and a control wire extending through the insertion tube to the instrument elevator, wherein translation of the control wire causes the instrument elevator to rotate, wherein the housing is transparent in X-ray images and comprises an instrument opening and a secondary opening opposite the instrument opening;

wherein the camera is positioned within the housing;

wherein the light emitting device is positioned within the housing with the optical axis aimed to illuminate at least a portion of the field of view of the camera;

wherein the instrument elevator comprises a radiopacity agent and a color; and wherein the color comprises an L* between 15 to 75, an a* between negative 10 to positive 10, and a b* between negative 10 to positive 10, as measured by a CIEL*a*b* colour code system.

* * * * *